United States Patent
Ceze et al.

(10) Patent No.: US 11,989,216 B2
(45) Date of Patent: May 21, 2024

(54) SYSTEMS AND METHODS FOR PROVIDING SIMILARITY-BASED RETRIEVAL OF INFORMATION STORED IN DNA

(71) Applicants: University of Washington, Seattle, WA (US); Microsoft Technology Licensing, LLC, Redmond, WA (US)

(72) Inventors: Luis Ceze, Seattle, WA (US); Karin Strauss, Seattle, WA (US); Georg Seelig, Seattle, WA (US); Callie Bee, Seattle, WA (US); Yuan-Jyue Chen, Seattle, WA (US)

(73) Assignees: University of Washington, Seattle, WA (US); Microsoft Technology Licensing, LLC, Redmond, WA (US)

(*) Notice: Subject to any disclaimer, the term of this patent is extended or adjusted under 35 U.S.C. 154(b) by 189 days.

(21) Appl. No.: 17/602,075

(22) PCT Filed: Apr. 9, 2020

(86) PCT No.: PCT/US2020/027545
§ 371 (c)(1),
(2) Date: Oct. 7, 2021

(87) PCT Pub. No.: WO2020/210544
PCT Pub. Date: Oct. 15, 2020

(65) Prior Publication Data
US 2022/0179891 A1    Jun. 9, 2022

Related U.S. Application Data
(60) Provisional application No. 62/831,533, filed on Apr. 9, 2019.

(51) Int. Cl.
G06F 16/33    (2019.01)
G16B 30/10    (2019.01)
G16B 40/20    (2019.01)

(52) U.S. Cl.
CPC ......... G06F 16/3346 (2019.01); G16B 30/10 (2019.02); G16B 40/20 (2019.02)

(58) Field of Classification Search
None
See application file for complete search history.

(56) References Cited

U.S. PATENT DOCUMENTS

| | | |
|---|---|---|
| 7,747,547 B1 | 6/2010 | Buturovic |
| 2002/0038185 A1 | 3/2002 | Kimura |

(Continued)

FOREIGN PATENT DOCUMENTS

| | | |
|---|---|---|
| CN | 105022935 A | 11/2015 |
| CN | 106504180 A | 3/2017 |

(Continued)

OTHER PUBLICATIONS

Maaskola, Jonas, and Nikolaus Rajewsky. "Binding site discovery from nucleic acid sequences by discriminative learning of hidden Markov models." Nucleic acids research 42.21 (2014): 12995-13011. (Year: 2014).*

(Continued)

*Primary Examiner* — Uyen T Le
(74) *Attorney, Agent, or Firm* — Christensen O'Connor Johnson Kindness PLLC

(57) ABSTRACT

In some embodiments, techniques are provided for conducting similarity-based searches using DNA. In some embodiments, sets of features that represent stored data sets are encoded in DNA sequences such that a hybridization yield between a molecule having a given stored DNA sequence and a molecule having a reverse complement of a DNA sequence that encodes a set of features that represent a query data set reflects an amount of similarity between the set of features that represent the query data set and the set of features encoded in the given stored DNA sequence. In some (Continued)

embodiments, machine learning techniques are used to determine the DNA sequence encoding. In some embodiments, machine learning techniques are used to predict hybridization yields between DNA molecules.

20 Claims, 19 Drawing Sheets

(56) References Cited

U.S. PATENT DOCUMENTS

| | | | |
|---|---|---|---|
| 2003/0077607 | A1 | 4/2003 | Hopfinger |
| 2004/0002816 | A1 | 1/2004 | Milosavljevic |
| 2011/0003301 | A1 | 1/2011 | Raymond |
| 2011/0099322 | A1 | 4/2011 | Brownell |
| 2015/0225774 | A1 | 8/2015 | Brevnov |
| 2016/0298175 | A1 | 10/2016 | Berka |
| 2016/0362720 | A1 | 12/2016 | Kim |
| 2017/0017436 | A1* | 1/2017 | Church .............. G11C 13/0016 |
| 2017/0091930 | A1 | 3/2017 | Kozuka |
| 2017/0337324 | A1 | 11/2017 | Church |
| 2018/0052953 | A1 | 2/2018 | Ganeshalingam |
| 2018/0265921 | A1 | 9/2018 | Chen |
| 2018/0285731 | A1 | 10/2018 | Heifets |
| 2018/0316569 | A1 | 11/2018 | Cilfone |
| 2019/0050495 | A1 | 2/2019 | Su |
| 2019/0105509 | A1 | 4/2019 | Tsai |
| 2019/0108310 | A1* | 4/2019 | Deforche ............... G16B 30/00 |
| 2019/0114511 | A1 | 4/2019 | Gao |
| 2019/0130280 | A1 | 5/2019 | Erden |
| 2019/0228081 | A1 | 7/2019 | Taig |
| 2021/0257054 | A1* | 8/2021 | Ryoo ..................... G16B 30/20 |
| 2022/0028497 | A1* | 1/2022 | Keung ................. C12Q 1/6816 |

FOREIGN PATENT DOCUMENTS

| | | |
|---|---|---|
| CN | 107437266 A | 12/2017 |
| CN | 109830263 A | 5/2019 |
| KR | 20090077536 A | 7/2009 |
| KR | 20160001455 A | 1/2016 |
| TW | 200745973 A | 12/2007 |
| WO | 2016020280 A1 | 2/2016 |
| WO | 2017083177 A1 | 5/2017 |
| WO | 2019081145 A1 | 5/2019 |
| WO | 2019144312 A1 | 8/2019 |

OTHER PUBLICATIONS

Wu, Tiee-Jian, Ying-Hsueh Huang, and Lung-An Li. "Optimal word sizes for dissimilarity measures and estimation of the degree of dissimilarity between DNA sequences." Bioinformatics 21.22 (2005): 4125-4132. (Year: 2005).*
Cherry, J. Michael. "Computer manipulation of DNA and protein sequences." Current Protocols in Molecular Biology 30.1 (1995): 7-7. (Year: 1995).*
Adleman, L.M. Molecular computation of solutions to combinatorial problems. Science 266(5187), 1021-1024 (Nov. 1994).
Andoni, A., Indyk, P. Near-optimal hashing algorithms for approximate nearest neighbor in high dimensions. Communications of the ACM 51(1), 117-122 (Jan. 2008).
Baum, E.B. Building an associative memory vastly larger than the brain. Science 268(5210), 583-585 (Apr. 1995).
Bee, C. et al. Content-Based Similarity Search in Large-Scale DNA Data Storage Systems. bioRxiv, May 27, 2020.
Bornholt, James, et al. "A DNA-based archival storage system." Proceedings of the Twenty-First International Conference on Architectural Support for Programming Languages and Operating Systems. 2016.
Cao, Zhen, and Shihua Zhang. "Probe efficient feature representation of gapped k-mer frequency vectors from sequences using deep neural networks." IEEE/ACM transactions on computational biology and bioinformatics 17.2 (2018): 657-667.
Carmean, D. et al. "DNA Data Storage and Hybrid Molecular-Electronic Computing," Proceedings of the IEEE, vol. 107, No. 1, Jan. 2019, pp. 63-72.
Ceze, L. et al. Molecular digital data storage using DNA. Nature Reviews Genetics. 20, pp. 456-466 (2019).
Chormunge, S. et al. Correlation based feature selection with clustering for high dimensional data. Journal of Electrical Systems and Information Technology. vol. 5, Issue 3, (2018) 542-549.
Church, G.M. et al. Next-generation digital information storage in DNA. Science. 337, 1628 (2012).
Dagher, G. G. et al. Data storage in cellular DNA: contextualizing diverse encoding schemes. Evolutionary Intelligence. vol. 14, pp. 331-343 (2021).
Dirks, Robert M., et al. "Thermodynamic analysis of interacting nucleic acid strands." SIAM review 49.1 (2007): 65-88.
Erlich, Y., Zielinski, D. DNA Fountain enables a robust and efficient storage architecture. Science 355(6328), pp. 950-954 (Mar. 2017).
Garzon, M.H., Bobba, K.V., Neel, A., "Efficiency and Reliability of Semantic Retrieval in DNA-Based Memories," In: J. Chen and J. Reif (Eds.) DNA Based Computers 2003: DNA9, LNCS 2943, pp. 157-169, 2004.
Goldman, N. et al. Towards practical, high-capacity, low-maintenance information storage in synthesized DNA. Nature. 494, pp. 77-80 (2013).
Grass, R. N. et al. Robust chemical preservation of digital information on DNA in silica with error-correcting codes. Angewandte Chemie Intl. Edition. 54, pp. 2552-2555 (2015).
Griffin, G., Holub, A., Perona, P., "Caltech-256 Object Category Dataset," (2007).
IDC: Where in the world is storage (2013), <http://www.idc.com/downloads/where_is_storage_infographic_243338.pdf>, 1 page.
Indyk, P., Motwani, R. Approximate nearest neighbors: Towards removing the curse of dimensionality. In: Proceedings of the Thirtieth Annual ACM Symposium on Theory of Computing. pp. 604-613. STOC '98, ACM, New York, NY, USA (1998). <https://doi.org/10.1145/276698.276876>, 10 pages.
Kawashimo, S., Ono, H., Sadakane, K., Yamashita, M. Dynamic Neighborhood Searches for Thermodynamically Designing DNA Sequence. In: Garzon M.H., Yan H. (eds) DNA Computing. DNA 2007: DNA 13, LNCS 4848, pp. 130-139, 2008.
Khan, A. et al. Principal Component Analysis-Linear Discriminant Analysis Feature Extractor for Pattern Recognition. IJCSI International Journal of Computer Science Issues, vol. 8, Issue 6, No. 2, Nov. 2011.
Krizhevsky, A. et al. ImageNet Classification with Deep Convolutional Neural Networks. Advance in Neural information processing systems 25 (2012) .<http://papers.nips.cc/paper/4824-imagenet-classification-with-deepconvolutional-neural-networks.pdf>, 9 pages.
Lee, V.T., Kotalik, J., d. Mundo, C.C., Alaghi, A., Ceze, L., Oskin, M. Similarity search on automata processors. In: 2017 IEEE International Par-allel and Distributed Processing Symposium (IPDPS). pp. 523-534 (May 2017).
Li, Heng. "Aligning sequence reads, clone sequences and assembly contigs with BWA-MEM." arXiv preprint arXiv:1303.3997 (2013).
Limbachiya, D. et al. Family of Constrained Codes for Archival DNA Data Storage. IEEE Communications Letters. vol. 22, Issue 10 (2018): 1972-1975.
Limbachiya, D. et al. On optimal family of codes for archival DNA storage. 2015 Seventh International Workshop on Signal Design and its Applications in Communications (IWSDA). IEEE. 2015.
Liu, F. et al. Deep Learning of Pre-Classification for Fast Image Retrieval. Proceedings of the 2018 International Conference on Algorithms, Computing and Artificial Intelligence. 2018.
Lopez Barrezueta, R. Repurposing DNA for information processing and storage. University of Washington Bioengineering Phd Thesis. 2018.
Malkov, Y. A. et al. Efficient and robust approximate nearest neighbor search using hierarchical navigable small world graphs. IEEE Transactions on Pattern Analysis and Machine Intelligence, vol. 42, No. 4, 2020, pp. 824-836.
Milenkovic, O. et al. DNA codes that avoid secondary structures. Proceedings. International Symposium on Information Theory (ISIT) 2005.

(56) References Cited

OTHER PUBLICATIONS

Min, X. et al. Chromatin accessibility prediction via convolutional long short-term memory networks with k-mer embedding. Bioinformatics, vol. 33, Issue 14, 2017, 192-1101.

Neel, A., Garzon, M., Penumatsa, P. Soundness and quality of semantic retrieval in DNA-based memories with abiotic data. In: 2004 Congress on Evolutionary Computation. pp. 1889-1895. IEEE (2004).

Neel, A., Garzon, M. Semantic Retrieval in DNA-Based Memories with Gibbs Energy Models. Biotechnology Progress 22(1), pp. 86-90 (2006).

Organick, L. et al. Random access in large-scale DNA data storage. Nature Biotechnology 36(3), pp. 242-248 (2018).

Organick, L., et al. Scaling up dna data storage and random access retrieval. bioRxiv (2017). <http://www.biorxiv.org/content/early/2017/03/07114553>, 14 pages.

Rashtchian, C. et al. Clustering Billions of Reads for DNA Data Storage. 31st Conference on Neural Information Processing Systems (NIPS 2017), Long Beach, CA, USA.

Rashtchian, C. New Algorithmic Tools for Distributed Similarity Search and Edge Estimation. University of Washington Computer Science and Engineering Phd Thesis, 2018.

Reif, J.H., LaBean, T.H., Pirrung, M., Rana, V.S., Guo, B., Kingsford, C., Wickham, G.S. Experimental Construction of Very Large Scale DNA Databases with Associative Search Capability. DNA Computing (2001).

Reif, J.H., LaBean, T.H. Computationally Inspired Biotechnologies: Improved DNA Synthesis and Associative Search Using Error-Correcting Codes and Vector-Quantization. DNA Computing (2000).

Salakhutdinov, R., Hinton, G. Semantic hashing. International Journal of Approximate Reasoning. 50(7), pp. 969-978 (2009).

Simonyan, Karen, and Andrew Zisserman. "Very deep convolutional networks for large-scale image recognition." arXiv preprint arXiv:1409.1556 (2014).

Song, W. et al. Codes With Run-Length and GC-Content Constraints for DNA-Based Data Storage. IEEE Communications Letters. vol. 22, Issue 10 (2018): 2004-2007.

Song, X. et al. Nucleic Acid Databases and Molecular-Scale Computing. ACS Nano 2019, 13(6) 6256-6268.

Stewart K. et al. (2018) A Content-Addressable DNA Database with Learned Sequence Encodings. In: Doty D., Dietz H. (eds) DNA 2018. Lecture Notes in Computer Science, vol. 11145. Springer, Cham, pp. 55-70, 2018.

Stuart, G. W. et al. Integrated gene and species phylogenies from unaligned whole genome protein sequences. Bioinformatics, vol. 18, Issue 1, 2002, pp. 100-108.

Sun, J. et al. Digital information storage on DNA in living organisms. Medical Research Archives. vol 7, issue 6, Jun. 2019.

Takahashi, C. N. et al. Demonstration of End-to-End Automation of DNA Data Storage. Scientific Reports vol. 9, Article No. 4998 (2019), pp. 1-5.

Tomek, K. J. et al. Driving the Scalability of DNA-Based Information Storage Systems. ACS Synth. Biol. 8(6) 1241-1248 (2019).

Tsaftaris, S.A., Hatzimanikatis, V., Katsaggelos, A.K. DNA Hybridization as a Similarity Criterion for Querying Digital Signals Stored in DNA Databases. In: 2006 IEEE International Conference on Acoustics Speed and Signal Processing. pp. II-1084-II-1087. IEEE (2006).

Tsaftaris, S.A., Katsaggelos, A.K., Pappas, T.N., Papoutsakis, T.E. DNA-based matching of digital signals. In: 2004 IEEE International Conference on Acoustics, Speech, and Signal Processing. pp. V-581-4. IEEE (2004).

Tulpan, D., Andronescu, M., Chang, S.B., Shortreed, M.R., Condon, A., Hoos, H.H., Smith, L.M. Thermodynamically based DNA strand design. Nucleic Acids Research 33(15), pp. 4951-4964 (Sep. 2005).

Wan, J., Wang, D., Hoi, S.C.H., Wu, P., Zhu, J., Zhang, Y., Li, J. Deep learning for content-based image retrieval: A comprehensive study. pp. 157-166 (2014).

Weiss, Y., Torralba, A., Fergus, R.: Spectral hashing. In: Proceedings of the 21st International Conference on Neural Information Processing Systems. pp. 1753-1760. NIPS'08, Curran Associates Inc., USA (2008), <http://dl.acm.org/citation.cfm?id=2981780.2981999>, 8 pages.

Wu, L.R., Wang, J.S., Fang, J.Z., R Evans, E., Pinto, A., Pekker, I., Boykin, R., Ngouenet, C., Webster, P.J., Beechem, J., Zhang, D.Y. Continuously tunable nucleic acid hybridization probes. Nature Methods 12(12), pp. 1191-1196 (2015).

Yazdi, S. et al. A rewritable, random-access DNA-based storage system. Sci. Rep. 5, 14138 (2015).

Yazdi, S. et al. Portable and Error-Free DNA-Based Data Storage. Scientific Reports vol. 7, Article No. 5011 (2017).

Zadeh, J.N., Steenberg, C.D., Bois, U.S., Wolfe, B.R., Pierce, M.B., Khan, A.R., Dirks, R.M., Pierce, N.A. NUPACK: Analysis and design of nucleic acid systems. Software News and Updates. Journal of Computational Chemistry 32(1), pp. 170-173, 2010.

Zhang, D.Y., Chen, S.X., Yin, P. Optimizing the specificity of nucleic acid hybridization. Nature Chemistry 4(3), pp. 208-214 (2012).

Zhang, Y. et al. Discerning novel splice junctions derived from RNA-seq alignment: a deep learning approach. BMC Genomics vol. 19, Article No. 971 (2018).

Aumueller, M. et al., ANN-Benchmarks, <http://ann-benchmarks.com> [Retrieved Oct. 6, 2021], 17 pages.

Facebookresearch/Faiss, MIT-licensed, <https://github.com/facebookresearch/faiss> [Retrieved Oct. 6, 2021], 5 pages.

Lyst/rpforest, <https://github.com/lyst/rpforest> [Retrieved Oct. 6, 2021], 7 pages.

Spotify/annoy <https://github.com/spotify/annoy> [Retrieved Oct. 6, 2021], 10 pages.

Overview of Open Images V6, <https://storage.googleapis.com/openimages/web/factsfigures.html> [Retrieved Oct. 6, 2021], 18 pages.

International Preliminary Report on Patentability dated Sep. 28, 2021, issued in corresponding International Application No. PCT/US2020/027545, filed Apr. 9, 2020, 21 pages.

International Search Report and Written Opinion dated Jul. 6, 2020, issued in corresponding International Application No. PCT/US2020/027545, filed Apr. 9, 2020, 24 pages.

\* cited by examiner

SYSTEMS AND METHODS FOR PROVIDING SIMILARITY-BASED RETRIEVAL OF INFORMATION STORED IN DNA

CROSS-REFERENCE TO RELATED APPLICATIONS

This application claims the benefit of Provisional Application No. 62/831,533, filed Apr. 9, 2019, the entire disclosure of which is hereby incorporated by reference for all purposes.

STATEMENT OF GOVERNMENT LICENSE RIGHTS

This invention was made with government support under Grant No. W911NF-18-2-0034, awarded by the Defense Advanced Research Projects Agency. The government has certain rights in the invention.

BRIEF SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In some embodiments, a method of performing a search for information similar to a query data set in a database that stores information in a plurality of storage nucleic acid molecules is provided. A set of features based on the query data set is determined. A query nucleic acid sequence is determined based on the set of features, wherein a degree of complementarity with the query nucleic acid sequence is correlated with a degree of similarity with the set of features. One or more query nucleic acid molecules are synthesized based on the query nucleic acid sequence. The one or more query nucleic acid molecules are contacted with the plurality of storage nucleic acid molecules. Storage nucleic acid molecules coupled to the query nucleic acid molecule are amplified to provide amplified storage nucleic acid molecules. Sequence data is generated based on the amplified storage nucleic acid molecules. The sequence data is translated into result data for the search.

In an embodiment, the method further comprises amplifying the one or more query nucleic acid molecules.

In an embodiment, synthesizing the one or more query nucleic acid molecules based on the query nucleic acid sequence includes coupling a biotin moiety to the query nucleic acid molecule, and the method further comprises contacting the query nucleic acid molecules with a plurality of magnetic beads coupled to a plurality of streptavidin moieties; and magnetically isolating the plurality of magnetic beads. Amplifying storage nucleic acid molecules coupled to the query nucleic acid molecule to provide amplified storage nucleic acid molecules includes amplifying storage nucleic acid molecules coupled to the plurality of magnetic beads.

In an embodiment, determining the set of features based on the query data set includes processing the query data set using an artificial neural network; and extracting activations from a hidden layer of the artificial neural network. Determining the set of features based on the query data set may further include conducting dimensionality reduction on the activations to obtain the set of features. Conducting dimensionality reduction on the activations to obtain the set of features may include performing principal component analysis (PCA) on the activations.

In an embodiment, processing the query data set using an artificial neural network includes processing the query data set using a VGG16 convolutional neural network. Extracting activations from the hidden layer of the artificial neural network may include extracting activations from an FC2 layer of the VGG16 convolutional neural network.

In an embodiment, determining the query nucleic acid sequence based on the set of features includes providing the set of features as input to a machine learning model trained to generate nucleic acid sequences designed to have degrees of complementarity that vary according to an amount of similarity between sets of features.

In an embodiment, synthesizing the one or more query nucleic acid molecules based on the query nucleic acid sequence includes synthesizing one or more molecules that include the query nucleic acid sequence and a reverse sequencing primer sequence.

In an embodiment, translating the sequence data into result data for the search includes using the sequence data to determine one or more identifier payload sequences; and using the one or more identifier payload sequences to retrieve one or more sets of result data for the search. Using the one or more identifier payload sequences to retrieve one or more sets of result data for the search may include using the identifier payload sequence as an amplification primer to amplify result nucleic acid molecules within a plurality of data nucleic acid molecules; generating result sequence data based on the amplified result nucleic acid molecules; and translating the result sequence data into the result data for the search. Using the one or more identifier payload sequences to retrieve one or more sets of result data for the search may include determining a result retrieval sequence based on the identifier sequence, wherein the result retrieval sequence includes a portion complementary to an identifier portion of desired result nucleic acid molecules; synthesizing one or more result retrieval nucleic acid molecules based on the result retrieval sequence; contacting the one or more result retrieval nucleic acid molecules with a plurality of data nucleic acid molecules; amplifying data nucleic acid molecules coupled to the one or more result retrieval nucleic acid molecules to provide amplified data nucleic acid molecules; generating sequence data based on the amplified data nucleic acid molecules; and translating the sequence data into the one or more sets of result data for the search.

In some embodiments, a computer-implemented method of conducting a similarity search using a nucleic acid data index is provided. A computing device determines a set of features based on a query data set. The computing device determines a query nucleic acid sequence based on the set of features. The computing device provides the query nucleic acid sequence for synthesizing into a query nucleic acid molecule. The computing device receives sequencing data for molecules retrieved from a plurality of storage nucleic acid molecules using the query nucleic acid molecule. The computing device decodes information stored in the sequencing data to obtain a search result.

In an embodiment, determining the set of features based on the query data set includes processing the query data set using an artificial neural network; and extracting activations from a hidden layer of the artificial neural network. Processing the query data set using the artificial neural network may include processing the query data using a VGG16 convolutional neural network. Extracting activations from the hidden layer of the artificial neural network may include extracting activations from an FC2 layer of the VGG16 convolutional neural network. Determining the set of features based on the query data set may include conducting dimensionality reduction on the extracted activations to determine the set of features. Conducting dimensionality reduction on the extracted activations to determine the set of features may include performing principal component analysis (PCA) on the activations.

In an embodiment, determining the query nucleic acid sequence based on the set of features includes providing the set of features as input to a machine learning model trained to generate nucleic acid sequences designed to have degrees of complementarity that vary according to an amount of similarity between sets of features. The amount of similarity between sets of features may be determined based on a Euclidean distance between the sets of features.

In an embodiment, decoding information stored in the sequencing data to obtain a search result includes determining, by the computing device, an identifier payload based on the sequencing data; determining, by the computing device, a result retrieval nucleic acid sequence based on the identifier payload; providing, by the computing device, the result retrieval nucleic acid sequence for synthesizing into a result retrieval nucleic acid molecule; receiving, by the computing device, sequencing data for molecules retrieved from a plurality of data nucleic acid molecules using the result retrieval nucleic acid molecule; and determining, by the computing device, a result data payload based on the sequencing data for the molecules retrieved from the plurality of data nucleic acid molecules. The result retrieval nucleic acid sequence may include a primer pair.

In some embodiments, a computer-implemented method of training one or more optimizable layers of a machine learning model to predict hybridization reaction yields is provided. For each pair of a plurality of pairs of nucleic acid sequences: a computing device generates features based on a first nucleic acid sequence of the pair and features based on a second nucleic acid sequence of the pair; the computing device provides the features as input to a set of one or more optimizable layers to generate an estimated reaction yield for the pair; the computing device generates a reverse complement sequence of the second nucleic acid sequence; the computing device determines a simulated reaction yield for the pair based on the first nucleic acid sequence and the reverse complement sequence; and the computing device determines a cross-entropy value between the estimated reaction yield and the simulated reaction yield. The computing device modifies parameters of the one or more optimizable layers to minimize a mean of the cross-entropy values.

In an embodiment, generating features based on the first nucleic acid sequence of the pair and features based on the second nucleic acid sequence of the pair includes determining a one-hot representation of the first nucleic acid sequence and a one-hot representation of the second nucleic acid sequence; determining outer products of k-mers of the one-hot representation of the first nucleic acid sequence and k-mers of the one-hot representation of the second nucleic acid sequence; and sliding the outer products over each adjacent pair of k-mers to generate a set of local matches. The k-mers may be 3-mers.

In an embodiment, generating features based on the first nucleic acid sequence of the pair and features based on the second nucleic acid sequence of the pair includes performing average pooling on the set of local matches to generate the features.

In an embodiment, providing the features as input to a set of one or more optimizable layers to generate an estimated reaction yield for the pair includes providing the features as input to one or more convolutional layers to generate a convolutional result. Providing the features as input to a set of one or more optimizable layers to generate an estimated reaction yield for the pair further may include determining a set of global averages based on the convolutional result. Providing the features as input to a set of one or more optimizable layers to generate an estimated reaction yield for the pair may include performing a regression on the set of global averages to determine the estimated reaction yield. Modifying parameters of the one or more optimizable layers to minimize the mean cross-entropy may comprise performing gradient descent to modify parameters of at least one of the convolution layers or the regression.

In an embodiment, determining the simulated reaction yield for the pair based on the first nucleic acid sequence and the reverse complement sequence comprises using a multi-stranded partition function to determine the simulated reaction yield for the first nucleic acid sequence and the reverse complement sequence.

In some embodiments, a computer-implemented method of predicting a hybridization reaction yield for a first nucleic acid sequence and a second nucleic acid sequence is provided. A computing device generates features based on the first nucleic acid sequence and the second nucleic acid sequence. The computing device provides the features as input to a set of one or more optimized layers. The set of one or more optimized layers have been trained to minimize a mean cross-entropy between estimated reaction yields and simulated reaction yields. The computing device provides an output of the set of one or more optimized layers as the predicted hybridization reaction yield.

In an embodiment, generating features based on the first nucleic acid sequence and the second nucleic acid sequence includes determining a one-hot representation of the first nucleic acid sequence and a one-hot representation of the second nucleic acid sequence; determining outer products of k-mers of the one-hot representation of the first nucleic acid sequence and k-mers of the one-hot representation of the second nucleic acid sequence; and sliding the outer products over each adjacent pair of k-mers to generate a set of local matches. The k-mers may be 3-mers.

In an embodiment, generating features based on the first nucleic acid sequence of the pair and features based on the second nucleic acid sequence of the pair further includes performing average pooling on the set of local matches to generate the features.

In an embodiment, providing the features as input to a set of one or more optimizable layers to generate an estimated reaction yield for the pair includes providing the features as input to one or more convolutional layers to generate a convolutional result. Providing the features as input to a set of one or more optimizable layers to generate an estimated reaction yield for the pair may include determining a set of global averages based on the convolutional result. Providing the features as input to a set of one or more optimizable layers to generate an estimated reaction yield for the pair may include performing a regression on the set of global averages to determine the estimated reaction yield.

In some embodiments, a computer-implemented method of training a machine learning model to generate nucleic acid sequences designed to have degrees of complementarity that vary according to an amount of similarity between sets of input data is provided. For each pair of a plurality of pairs of sets of input data, the pairs of sets of input data each including a first set of input data and a second set of input data: a computing device determines a first set of features based on the first set of input data and a second set of features based on the second set of input data; the computing device determines a logical similarity between the first set of features and the second set of features; the computing device provides the first set of features and the second set of features as input to the machine learning model to generate a first nucleic acid sequence and a second nucleic acid sequence; the computing device determines a molecular similarity between the first nucleic acid sequence and the second nucleic acid sequence; and the computing device determines a cross-entropy value between the logical similarity and the molecular similarity. The computing device modifies parameters of the machine learning model to minimize a mean of the cross-entropy values.

In an embodiment, determining the molecular similarity between the first nucleic acid sequence and the second nucleic acid sequence includes providing the first nucleic acid sequence and the second nucleic acid sequence as inputs to a machine learning model trained to predict hybridization reaction yields.

In an embodiment, determining the molecular similarity between the first nucleic acid sequence and the second nucleic acid sequence includes determining a mean cosine distance between the first nucleic acid sequence and the second nucleic acid sequence.

In an embodiment, determining the logical similarity between the first set of features and the second set of features includes determining a Euclidean distance between the first set of features and the second set of features; and comparing the Euclidean distance to a similarity threshold.

In an embodiment, the sets of input data are images, text, or video. In an embodiment wherein the sets of input data are images, determining the first set of features based on the first set of input data and a second set of features based on the second set of input data may include providing the first set of input data and the second set of input data to a VGG16 convolutional neural network; and extracting activations from an FC2 layer of the VGG16 convolutional neural network. Determining the first set of features based on the first set of input data and a second set of features based on the second set of input data may include conducting dimensionality reduction on the activations to obtain the first set of features and the second set of features. Conducting dimensionality reduction on the activations to obtain the first set of features and the second set of features may include performing principal component analysis (PCA) on the activations.

In an embodiment, modifying parameters of the machine learning model to minimize a mean of the cross-entropy values includes performing gradient descent to modify the parameters of the machine learning model.

For any of the above described embodiments, a computing device or computing system may be provided that is configured to perform the described method. Likewise, for any of the above described embodiments, a computer-readable medium may be provided having computer-executable instructions stored thereon that, in response to execution by a computing system, cause the computing system to perform the actions of the described method.

In some embodiments, a system for performing a similarity search using nucleic acids is provided. The system comprises a nucleic acid synthesizer configured to synthesize nucleic acid molecules; a nucleic acid sequencer configured to generate a signal based upon a sequence of a nucleic acid; a plurality of storage nucleic acid molecules, and a controller operatively coupled to the nucleic acid synthesizer and the nucleic acid sequencer. Each of the plurality of storage nucleic acid molecules includes a payload sequence associated with a data object; and a target sequence based on a set of features derived from the data object. The controller includes logic that, in response to execution by the controller, causes the system to perform operations including: converting a received query data set into a query nucleic acid sequence, the query nucleic acid sequence comprising a query sequence based on a set of features based on the query data set, wherein a degree of complementarity of the query sequence and a target sequence is based upon a Euclidean distance between the set of features based on the query data set and the set of features derived from the data object; synthesizing a query nucleic acid molecule based on the query nucleic acid sequence with the nucleic acid synthesizer; contacting the query nucleic acid molecule with the plurality of storage nucleic acid molecules; amplifying storage nucleic acid molecules coupled to the query nucleic acid molecule to provide amplified storage nucleic acid molecules; and generating sequence data with the nucleic acid sequencer based on the amplified storage nucleic acid molecules.

In an embodiment, a greater degree of complementarity between the query nucleic acid sequence and the target sequence corresponds to a shorter Euclidean distance between the set of features based on the query data set and the set of features derived from the data object.

In an embodiment, the system further comprises a plurality of magnetic beads coupled to a plurality of streptavidin moieties; the query nucleic acid molecule further comprises a biotin moiety coupled to the query sequence; and the controller further includes logic that, in response to execution by the controller, causes the system to perform operations including: contacting the query nucleic acid molecule with the plurality of magnetic beads; magnetically isolating the plurality of magnetic beads; and amplifying storage nucleic acid molecules coupled to the plurality of magnetic beads.

In an embodiment, amplifying storage nucleic acid molecules includes performing a polymerase chain reaction, and the storage nucleic acid molecules include a forward primer and a reverse primer. The query sequence may include one or more base pairs complementary to base pairs of one or more of the forward primer and the reverse primer.

In an embodiment, the payload sequence encodes an identifier usable to retrieve the data object.

In an embodiment, the payload sequence encodes the data object.

In an embodiment, the controller includes logic that, in response to execution by the controller, causes the system to perform operations including synthesizing a storage nucleic acid molecule with the nucleic acid synthesizer. The storage nucleic acid molecule comprises a payload sequence based on a data object; and a target sequence based on a set of features derived from the data object.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Figure 1:
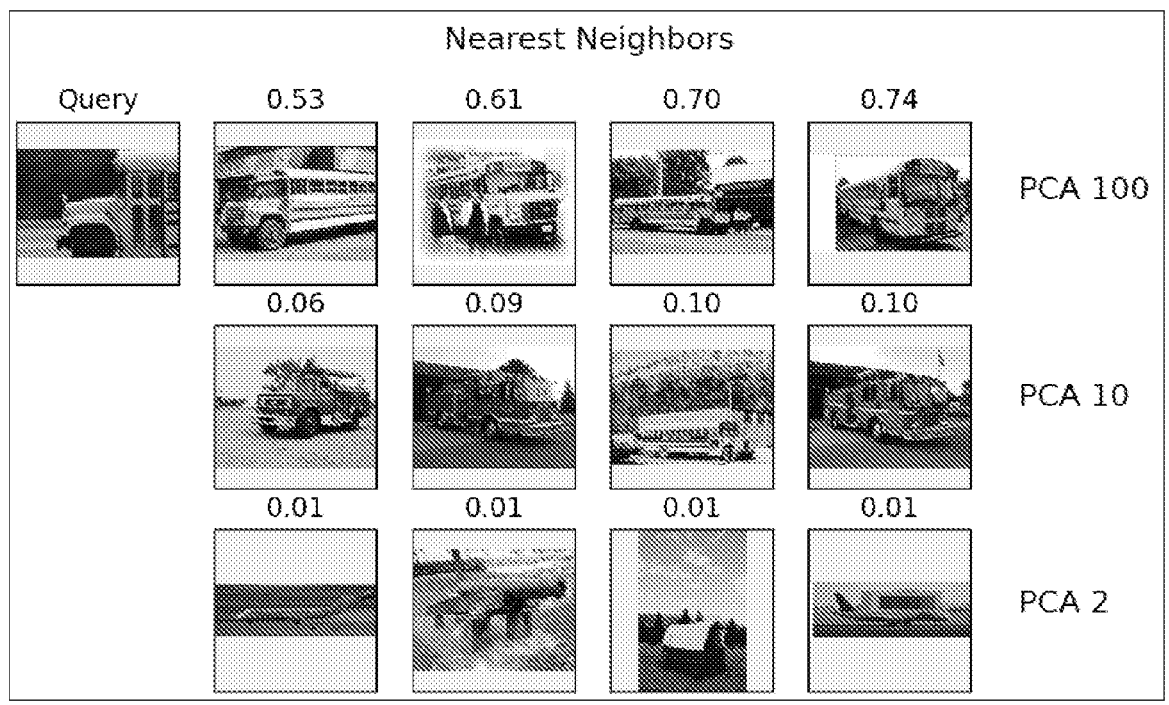
FIG. 1 illustrates a pair of sample similarity search image queries from the Caltech-256 dataset, showing the four nearest neighbors to a query image in three different feature spaces.
Figure 1:
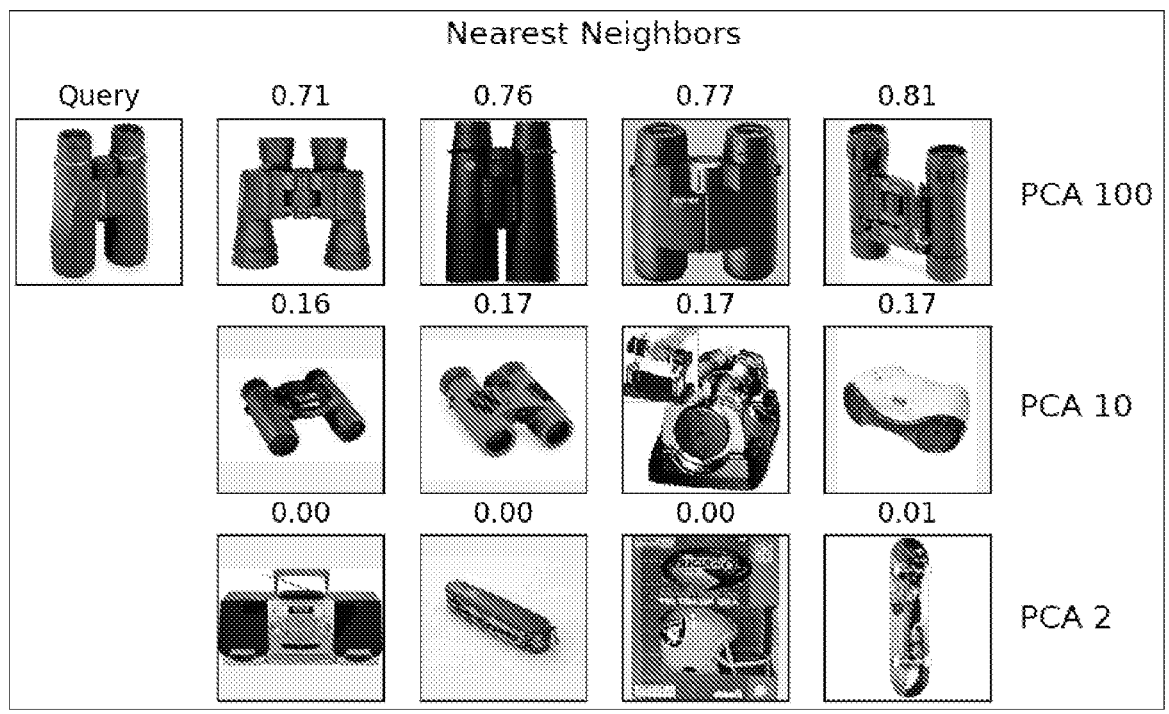

DNA-based databases were first proposed over twenty years ago by Baum. Recent demonstrations of their practicality have generated a renewed interest into researching related theory and applications. Some of these recent demonstrations of DNA storage have used key-based random access for their retrieval schemes. While this does allow for the storage of massive amounts of data that can be retrieved by random access, the exact key for a single desired result must be used to retrieve a single result. In any data storage technique, it is desirable to be able to perform content-based associative searches, where results that are similar to a query but do not necessarily exactly match the query may be retrieved from storage. In some embodiments of the present disclosure, the properties of DNA are leveraged in order to provide content-based associative searches over data stored in DNA.

The present disclosure provides multiple advances in the field of DNA storage. For example, in some embodiments, a strand design that is optimized for associative search is provided. As another example, in some embodiments, a sequence encoder that is configured to preserve similarity between data sets, such that a query sequence generated for a first data set will retrieve data sets similar to the first data set from DNA-based storage. As yet another example, in some embodiments, techniques for rapidly estimating a hybridization yield between two DNA sequences are provided.

The problem posed by a "similarity search" or an "associative search" is to retrieve data sets from storage that are similar in content to a query data set. As used herein, "data set" refers to a set of data that is collectively stored, searched for, and retrieved as a unit. One non-limiting example of a data set is an image file including but not limited to a GIF file, a JPEG file, or a PNG file. Another non-limiting example of a data set is a video file including but not limited to an MPEG file. Another non-limiting example of a data set is a document, including but not limited to a plaintext document, a code document, a word processing document, or a web page. In some embodiments, a data set may be any collection of data from which features can be extracted for performing a similarity search. The term "data set" and terms referring to any individual type of data set, including but not limited to "image" or "image file," may be used interchangeably herein without limiting the description to any particular kind of data set.

For media data sets such as text, images, and video, this can be a difficult task. In some systems, each data set is converted into a vector-space representation using either a hand-crafted embedding or one learned via a machine learning model such as a neural network. These feature vectors can then be compared to each other using metrics that include Euclidean distance, where similar data sets will tend to be close together in feature-space. Using such techniques, a similarity search can be reduced to a k-nearest-neighbor or R-near-neighbor search.

Feature vectors that are effective for similarity search tend to be high-dimensional, which is shown in FIG. 1. FIG. 1 illustrates a pair of sample similarity search image queries from the Caltech-256 data collection, showing the four nearest neighbors to a query image in three different feature spaces. Each neighbor is annotated with its Euclidean distance to the query in that space. The visual features of each image in the dataset were extracted using VGG16, a publicly available convolutional neural network (CNN) trained on an image classification task. The features were extracted using the 4096-dimensional activations from the FC2 layer, an intermediate layer in VGG16 whose activations have been shown to be effective in content-based image retrieval tasks. These features were reduced down to 100, 10, and 2 dimensions using principal component analysis (PCA). The nearest neighbors in each of these subspaces with respect to Euclidean distance are shown to the right of each query. Qualitatively, the nearest neighbors higher-dimensional spaces appear more similar to the query than the nearest neighbors in lower-dimensional spaces.

When feature vectors have hundreds of dimensions, the well-known "curse of dimensionality" can defeat efficient indexing schemes. In the worst case, every item in the database would be examined to find all images within a certain distance threshold. Relaxations of the search problem that allow for errors or omissions may result in much faster lookups, using algorithms such as locality-sensitive hashing (LSH). Looking toward a future where zettabytes of data are generated every year, even techniques such as LSH that reduce the amount of data that needs to be inspected by orders of magnitude will still burden traditional computer-readable storage with a tremendous number of I/O requests to a massive storage infrastructure, outstripping the time and energy cost of the feature vector distance computation itself.

Computer architects have noticed that the power required to move data from the storage device to the compute unit can be reduced by moving the compute substrate closer to the storage substrate. This class of techniques is broadly called "near-data" processing. "Adleman-style" DNA computing can be thought of as an extreme version of near-data processing: each DNA strand is designed to both store and process information. That is, one could consider that the compute and storage substrates to both be provided by the DNA strands.

Like Adleman's original solution to the Hamiltonian Path problem, this style of parallel processing requires exponential amounts of DNA to solve combinatorial problems. However, for less computationally intense problems like similarity search, the amount of DNA required is much less: if each of N items in the database is mapped to a single "target" molecule, then N identical copies of a "query" molecule are sufficient to react with every item in the database. If the query is equipped with a biotin tail and designed to hybridize only with relevant data, then relevant items can be "fished out" of the database using streptavidin-coated magnetic beads. This amounts to an extremely high-bandwidth parallel search, in the vein of near-data processing techniques. Furthermore, because PCR can make exponentially many copies of the query molecule, the amount of DNA that needs to be directly synthesized is minimal. This makes DNA-based similarity search especially appealing in the zettabyte-yottabyte future.

In some embodiments of the present disclosure, a data storage is provided for storing and retrieving metadata. Instead of storing sequences that contain the complete data set, each data set is associated with a sequence that contains the semantic features used for content-based retrieval, as well as a pointer to the data set in another database (which could either be a traditional data store or DNA-based storage). To take advantage of the near-data processing capabilities of DNA, the present disclosure allows each element in the database to both store and process data. In order to separate these two purposes, each data set stored by the system is associated with two sequences: a first sequence that stores an identifier unique to the data set, and a second sequence that is generated from the semantic features of the data set. The second sequence is designed as a locus for a hybridization probe. The first sequence is not an "active" site, but is rather the metadata information to be retrieved by the search. For example, the first sequence may encode an address of the data set in another storage location that stores the data set's complete data.

One simple way to retain the association between the identifier sequence and the feature sequence in a DNA storage system is to place them on the same strand of DNA. However, this association can cause unwanted secondary structures on longer strands, and can result in cross-talk if a query sequence reacts with a potential target's identifier sequence instead of its features sequence.

Figure 2:
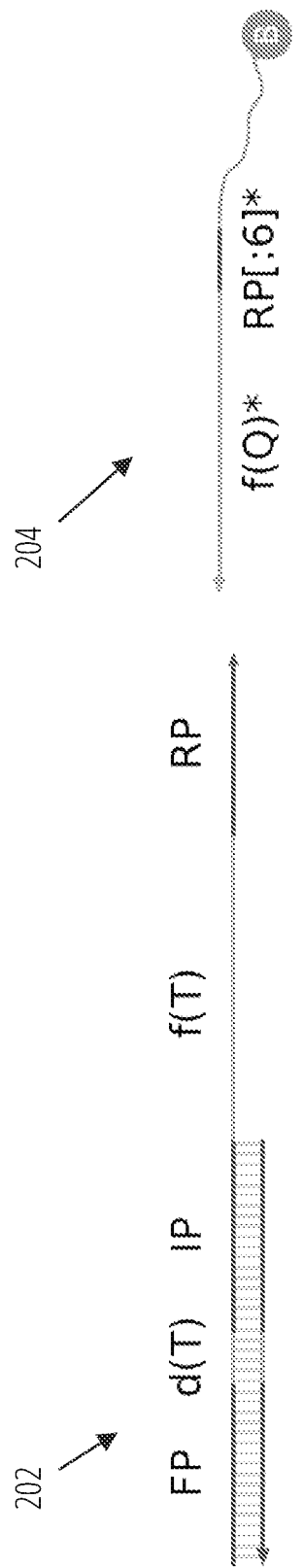
FIG. 2 illustrates a non-limiting example embodiment of a strand design that addresses issues of unwanted cross-talk and secondary structures while providing capabilities for similarity-based information retrieval according to various aspects of the present disclosure.

FIG. 2 illustrates a non-limiting example embodiment of a strand design that addresses issues of unwanted cross-talk and secondary structures while providing capabilities for similarity-based information retrieval according to various aspects of the present disclosure. The storage nucleic acid molecule 202 is synthesized single-stranded, but is made partially double stranded using a single-step PCR reaction starting from IP (the "internal primer"), which is conserved across all storage molecules in the system. This process covers up the IP region, the identifier sequence associated with the data (indicated as "d(T)" in FIG. 2), and the forward primer (indicated as "FP" in FIG. 2), which is another conserved region used to prepare samples for sequencing. This leaves the feature sequence (indicated as "f(T)" in FIG. 2) and the conserved reverse sequencing primer (indicated as "RP" in FIG. 2) available to interact with a query molecule.

To execute a query Q, a query nucleic acid molecule 204 is used. FIG. 2 shows that the query nucleic acid molecule 204 is biotinylated. The biotinylated query strand is mixed with the prepared storage nucleic acid molecules 202. Because the query and target feature sequences are designed to be imperfect matches, the query nucleic acid molecule 204 also includes the reverse complement of the first six bases of RP (indicated as "RP[:6]*" in FIG. 2). This exact match sequence is designed to prevent misalignments and ensure that hybridization only depends on the interaction between f(T) and f(Q). The query and storage molecules are annealed, and then streptavidin-coated magnetic beads are added to pull down storage molecules that have hybridized with the queries. The resulting filtered storage molecules may be amplified using FP and RP, then sequenced to retrieve the data region d(T) associated with each storage molecule.

Figure 3:
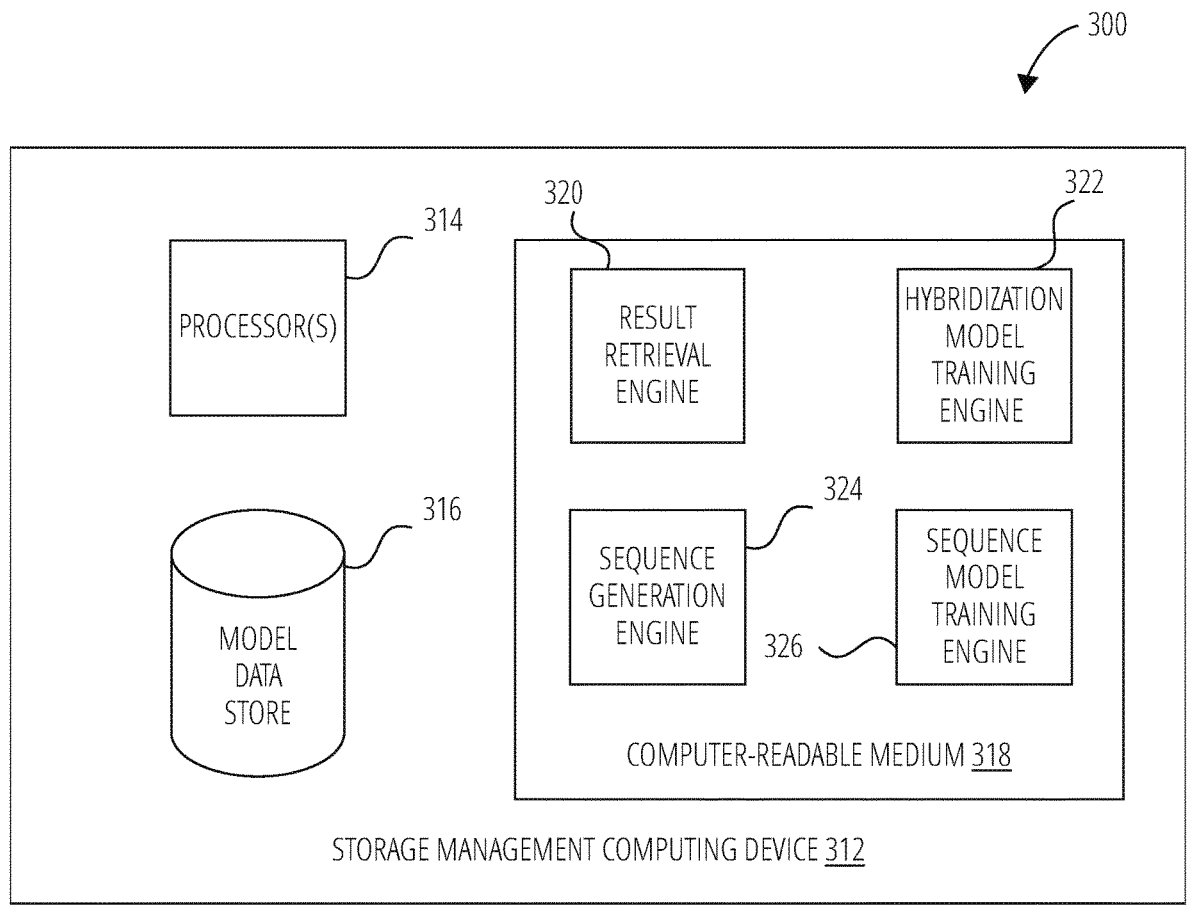
FIG. 3 is a block diagram that illustrates a non-limiting example embodiment of a system according to various aspects of the present disclosure.
Figure 3:
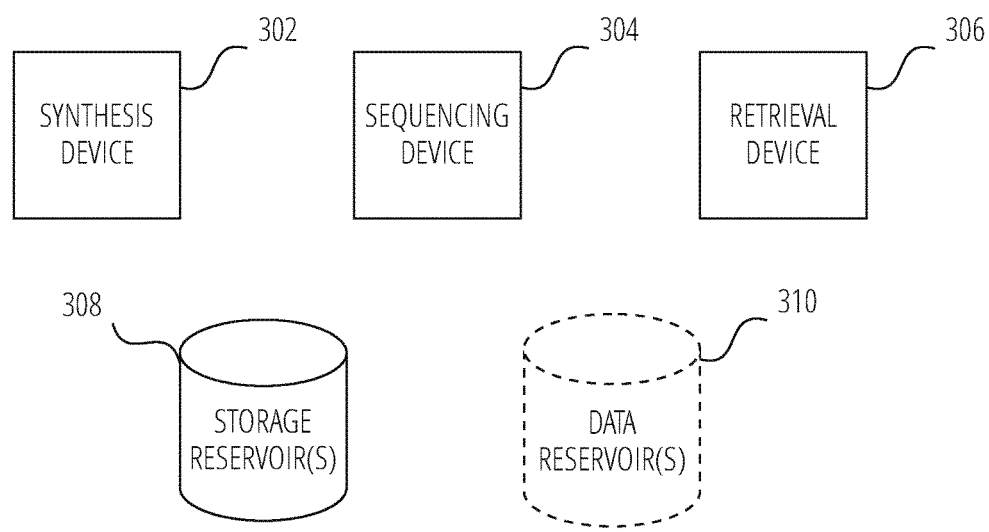

FIG. 3 is a block diagram that illustrates a non-limiting example embodiment of a system according to various aspects of the present disclosure. As illustrated, the system 300 is configured to store data sets, receive query data sets, and retrieve stored data sets that are similar to the query data sets. The illustrated system 300 is also configured to train and use machine learning models to generate sequences with similarities that correlate to similarities between data sets, and to train and use machine learning models that estimate hybridization reaction yields between pairs of DNA sequences.

As shown, the system 300 includes a synthesis device 302, a sequencing device 304, a retrieval device 306, and a storage management computing device 312.

In some embodiments, the synthesis device 302 includes one or more devices capable of generating a synthetic DNA molecule based on a specified sequence of nucleotides using any suitable technique, including but not limited to oligonucleotide synthesis, annealing based connection of oligonucleotides, or any other suitable technique.

In some embodiments, the sequencing device 304 includes one or more devices that are capable of determining a sequence of nucleotides that make up a DNA molecule. One non-limiting example of a sequencing device 304 is the NextSeq 550 System from Illumina, Inc., though other devices and other sequencing techniques may be used.

In some embodiments, the retrieval device 306 includes one or more devices for transferring material between various reservoirs and other devices, and for performing other physical operations on the material. For example, the retrieval device 306 may include one or more pipettes or dispensers configured to transfer material from the synthesis device 302 to a storage reservoir 308, from a storage reservoir 308 to the sequencing device 304, from reservoirs of reagents to a reaction container, or any other suitable transfer. As another example, the retrieval device 306 may include devices for isolating magnetic beads, including but not limited to a magnet or a centrifuge. As yet another example, the retrieval device 306 may include one or more thermocyclers (or devices for transporting objects into or out of a thermocycler) for performing annealing processes. In some embodiments, the retrieval device 306 may be fully automated. In some embodiments, at least some of the actions descried as being performed by the retrieval device 306 may be performed manually.

As shown, the storage management computing device 312 includes one or more processor(s) 314, a model data store 316, and a computer-readable medium 318. In some embodiments, the processor(s) 314 may include one or more commercially available general-purpose computer processors, each of which may include one or more processing cores. In some embodiments, the processor(s) 314 may also include one or more special-purpose computer processors, including but not limited to one or more processors adapted for efficiently performing machine learning tasks. In some embodiments, the model data store 316 is configured to store one or more machine learning models for use by the components of the storage management computing device 312.

As used herein, "computer-readable medium" refers to a removable or nonremovable device that implements any technology capable of storing information in a volatile or nonvolatile manner to be read by a processor of a computing device, including but not limited to: a hard drive; a flash memory; a solid state drive; random-access memory (RAM); read-only memory (ROM); a CD-ROM, a DVD, or other disk storage; a magnetic cassette; a magnetic tape; and a magnetic disk storage.

As used herein, "data store" refers to any suitable device configured to store data for access by a computing device. One example of a data store is a highly reliable, high-speed relational database management system (DBMS) executing on one or more computing devices and accessible over a high-speed network. Another example of a data store is a key-value store. However, any other suitable storage technique and/or device capable of quickly and reliably providing the stored data in response to queries may be used, and the computing device may be accessible locally instead of over a network, or may be provided as a cloud-based service. A data store may also include data stored in an organized manner on a computer-readable storage medium, such as a hard disk drive, a flash memory, RAM, ROM, or any other type of computer-readable storage medium. One of ordinary skill in the art will recognize that separate data stores described herein may be combined into a single data store, and/or a single data store described herein may be separated into multiple data stores, without departing from the scope of the present disclosure.

As illustrated, the computer-readable medium 318 includes stored thereon instructions that, in response to execution by the processor(s) 314, cause the storage management computing device 312 to provide a result retrieval engine 320, a hybridization model training engine 322, a sequence generation engine 324, and a sequence model training engine 326. In some embodiments, the result retrieval engine 320 is configured to receive a query data set from a requesting computing device and to work with the other components of the system 300 to provide results corresponding to the query data set. In some embodiments, the hybridization model training engine 322 is configured to train a machine learning model to estimate hybridization yields for pairs of DNA sequences. In some embodiments, the sequence model training engine 326 is configured to train a machine learning model to generate DNA sequences that represent features of a data set, wherein similarity between DNA sequences represents similarity between the features of the data sets. In some embodiments, the sequence generation engine 324 is configured to use a model trained by the sequence model training engine 326 to generate DNA sequences for data sets. Further details about the functionality of each of these components are provided below.

As used herein, "engine" refers to logic embodied in hardware or software instructions, which can be written in a programming language, such as C, C++, COBOL, JAVA™, PHP, Perl, HTML, CSS, JavaScript, VBScript, ASPX, Microsoft .NET™, Go, Python, and/or the like. An engine may be compiled into executable programs or written in interpreted programming languages. Software engines may be callable from other engines or from themselves. Generally, the engines described herein refer to logical modules that can be merged with other engines, or can be divided into sub-engines. The engines can be implemented by logic stored in any type of computer-readable medium or computer storage device and be stored on and executed by one or more general purpose computers, thus creating a special purpose computer configured to provide the engine or the functionality thereof. The engines can be implemented by logic programmed into an application-specific integrated circuit (ASIC), a field-programmable gate array (FPGA), or another hardware device.

The illustrated system 300 also includes one or more storage reservoir(s) 308 and one or more data reservoir(s) 310. In some embodiments, the one or more storage reservoir(s) 308 include a plurality of different storage nucleic acid molecules 202 that store identifiers of data sets. In some embodiments, the one or more data reservoir(s) 310 include a plurality of different data nucleic acid molecules. In some embodiments, the data nucleic acid molecules store a plurality of data sets, and a given data set can be retrieved using the identifier retrieved from the storage nucleic acid molecules 202. The data reservoir(s) 310 are illustrated as optional because, in some embodiments, the identifier retrieved from the storage nucleic acid molecules 202 may be used to retrieve the data set in some other way, including but not limited to from a traditional data store. In such embodiments where the data reservoir(s) 310 are not used, the benefits of near-data processing can be realized for the similarity search, even if the massive storage capabilities provided by DNA storage of the data sets themselves is not utilized.

The system 300 may include multiple other components, including but not limited to the aforementioned requesting computing device and thermocycler, a network that communicatively couples one or more of the components of the system 300 together, reservoirs for reagents, and so on. Though those commonly known components (and others) may be part of some embodiments of the system 300, they have not been illustrated in FIG. 3 for the sake of clarity and brevity.

The system 300 is illustrated as being capable of processing queries, training machine learning models, and using machine learning models for ease of discussion. However, in some embodiments, the system 300 may not be configured to do all of these tasks, and therefore may not include all of the illustrated components. For example, in some embodiments, the system 300 may use machine learning models generated by another system, but may not train them, and so may be missing the hybridization model training engine 322 and the sequence model training engine 326. As another example, in some embodiments, the system 300 may train machine learning models, but may not process queries, in which case the hybridization model training engine 322 and the sequence model training engine 326 may be the only components present on the computer-readable medium 318, and the synthesis device 302, sequencing device 304, and retrieval device 306 may not be present.

Figure 4:
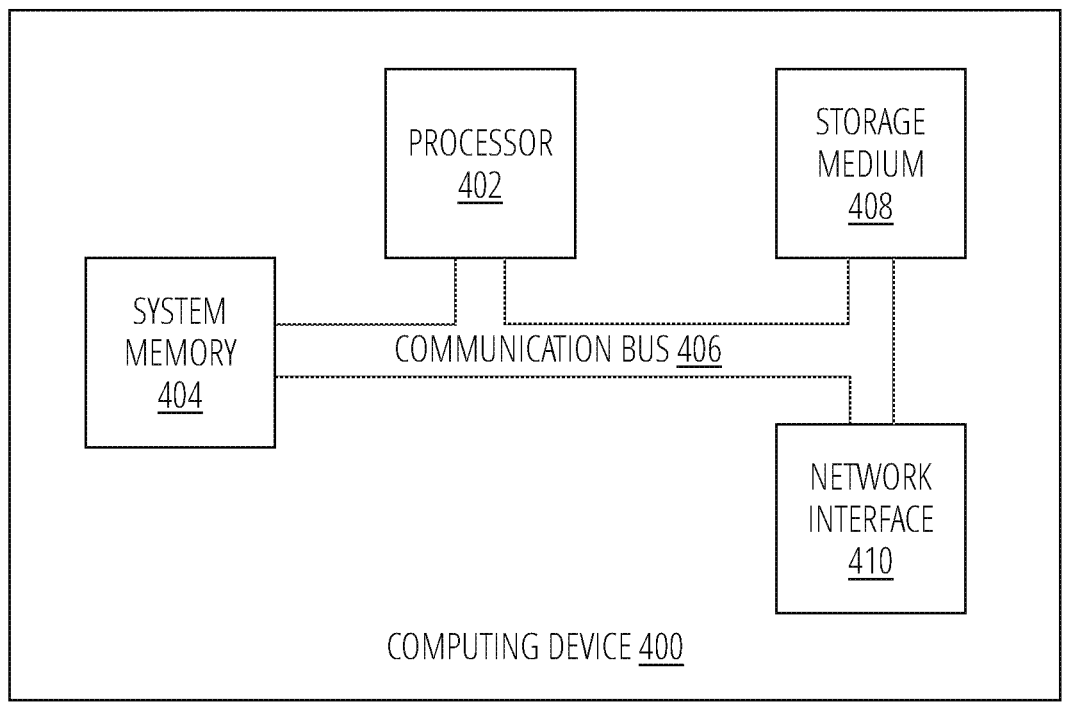
FIG. 4 is a block diagram that illustrates a non-limiting example embodiment of a computing device appropriate for use as a computing device with embodiments of the present disclosure.

FIG. 4 is a block diagram that illustrates aspects of an exemplary computing device 400 appropriate for use as a computing device of the present disclosure. The exemplary computing device 400 describes various elements that are common to many different types of computing devices, including but not limited to a laptop computing device, a server computing device, a tablet computing device, a smartphone computing device, an embedded computing device, and a computing device that is part of a cloud computing system. Some embodiments of a computing device may be implemented in or may include an application-specific integrated circuit (ASIC), a field-programmable gate array (FPGA), or other customized device. Moreover, those of ordinary skill in the art and others will recognize that the computing device 400 may be any one of any number of currently available or yet to be developed devices.

In its most basic configuration, the computing device 400 includes at least one processor 402 and a system memory 404 connected by a communication bus 406. Depending on the exact configuration and type of device, the system memory 404 may be volatile or nonvolatile memory, such as read only memory ("ROM"), random access memory ("RAM"), EEPROM, flash memory, or similar memory technology. Those of ordinary skill in the art and others will recognize that system memory 404 typically stores data and/or program modules that are immediately accessible to and/or currently being operated on by the processor 402. In this regard, the processor 402 may serve as a computational center of the computing device 400 by supporting the execution of instructions.

As further illustrated in FIG. 4, the computing device 400 may include a network interface 410 comprising one or more components for communicating with other devices over a network. Embodiments of the present disclosure may access basic services that utilize the network interface 410 to perform communications using common network protocols. The network interface 410 may also include a wireless network interface configured to communicate via one or more wireless communication protocols, such as Wi-Fi, 2G, 3G, LTE, WiMAX, Bluetooth, Bluetooth low energy, and/or the like. As will be appreciated by one of ordinary skill in the art, the network interface 410 illustrated in FIG. 4 may represent one or more wireless interfaces or physical communication interfaces described and illustrated above with respect to particular components of the computing device 400.

In the exemplary embodiment depicted in FIG. 4, the computing device 400 also includes a storage medium 408. However, services may be accessed using a computing device that does not include means for persisting data to a local storage medium. Therefore, the storage medium 408 depicted in FIG. 4 is represented with a dashed line to indicate that the storage medium 408 is optional. In any event, the storage medium 408 may be volatile or nonvolatile, removable or nonremovable, implemented using any technology capable of storing information such as, but not limited to, a hard drive, solid state drive, CD ROM, DVD, or other disk storage, magnetic cassettes, magnetic tape, magnetic disk storage, and/or the like.

Suitable implementations of computing devices that include a processor 402, system memory 404, communication bus 406, storage medium 408, and network interface 410 are known and commercially available. For ease of illustration and because it is not important for an understanding of the claimed subject matter, FIG. 4 does not show some of the typical components of many computing devices. In this regard, the computing device 400 may include input devices, such as a keyboard, keypad, mouse, microphone, touch input device, touch screen, tablet, and/or the like. Such input devices may be coupled to the computing device 400 by wired or wireless connections including RF, infrared, serial, parallel, Bluetooth, Bluetooth low energy, USB, or other suitable connections protocols using wireless or physical connections. Similarly, the computing device 400 may also include output devices such as a display, speakers, printer, etc. Since these devices are well known in the art, they are not illustrated or described further herein.

In order to implement the similarity search and retrieval method 1200 discussed below, a mapping from data sets to feature domains is used such that a query molecule will retrieve relevant targets from storage. To simplify this task, all data sets stored in the system 300 are pre-processed by transforming them into the sets of features, and then encoding the sets of features in a nucleotide sequence. The nucleotide sequences are used as the f(T) portion of the storage nucleic acid molecule 202 for each stored data set. The encoding technique is then used in the method 1200, as discussed below, to transform the set of features corresponding to a query data set to create a query nucleic acid molecule. Typically, the encoding technique utilizes a machine learning model that is trained to encode sets of features in nucleic acid sequences that have hybridization yields that vary based on similarities of the sets of features.

Figure 5:
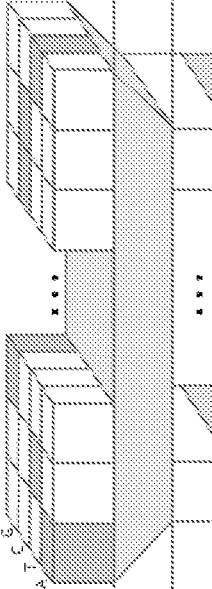
FIG. 5 illustrates a non-limiting example embodiment of a machine learning model architecture for encoding data sets into nucleic acid sequences according to various aspects of the present disclosure.

FIG. 5 illustrates a non-limiting example embodiment of a machine learning model architecture for encoding data sets into nucleic acid sequences according to various aspects of the present disclosure. The machine learning model begins with two convolutional layers, where each input dimension is processed independently with a shared set of weights. This preserves some of the "element-wise" structure of the Euclidean distance used to calculate the similarity label. The first convolutional layer has a sine-function activation, inspired by spectral hashing (a method for transforming an input feature space into a binary address space). The second convolutional layer uses the ReLU function to allow the outputs to be further apart. Since the input dimensions do not have a spatial interpretation, the convolutional layers are capped with a set of fully connected weights to the four-channel sequence output, such that each input dimension's activation map is given a chance to influence each base in all positions. A ReLU activation followed by a softmax activation gives the approximate one-hot representation discussed above.

Figure 6:
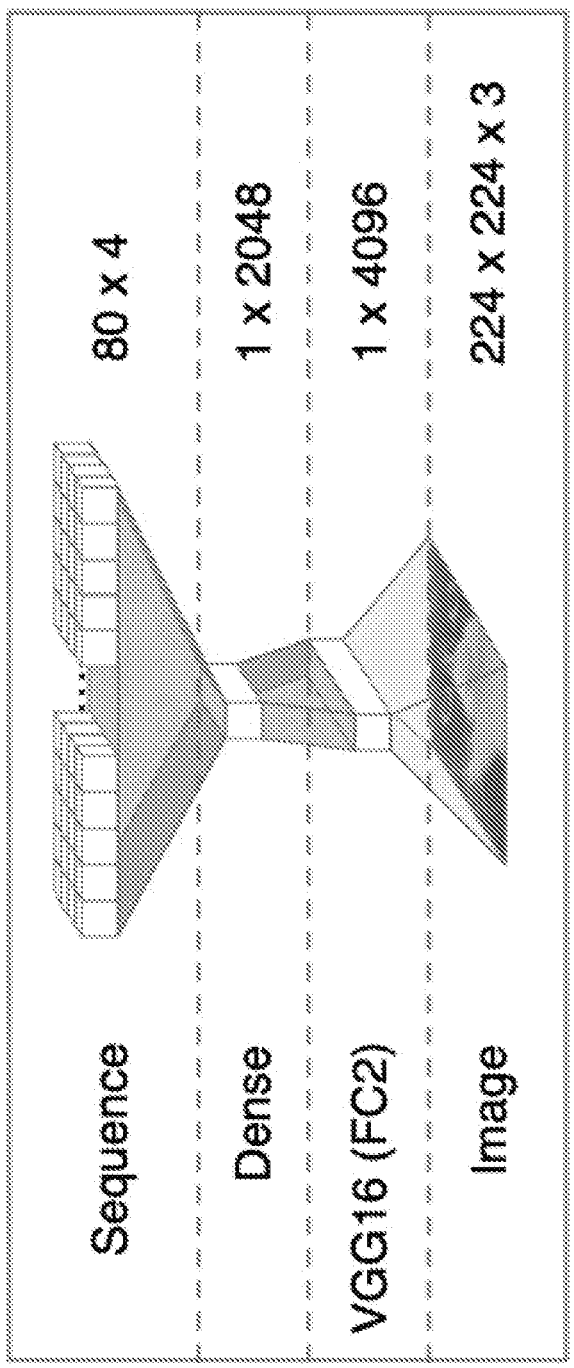
FIG. 6 illustrates another non-limiting example embodiment of a machine learning model architecture for encoding data sets into nucleic acid sequences according to various aspects of the present disclosure.

FIG. 6 illustrates another non-limiting example embodiment of a machine learning model architecture for encoding data sets into nucleic acid sequences according to various aspects of the present disclosure. In the embodiment illustrated in FIG. 6, the 4096-dimensional FC2 layer vectors of VGG16 are fed into a 2048-dimensional hidden layer with a rectified linear (ReLU) activation, followed by an output layer with a one-hot sequence representation that is 80 nucleotides in length. In this representation, each sequence position has four channels, one for each base. A softmax activation function is applied that forces each position's channels to sum to 1. The DNA sequence can be read off by picking the channel with the maximum activity at each position. As shown, the 2048-dimensional hidden layer and the output layer are optimizable layers (they are layers that have weights that change during training of the machine learning model). This one-hot representation can produce indeterminate bases (for example, if all four channels at a position have a value of 0.25. Because of this, a regularization is applied during training to minimize the entropy at each position. This encourages each position to have a well-defined maximum, which improves the accuracy of the yield predictor.

Figure 7:
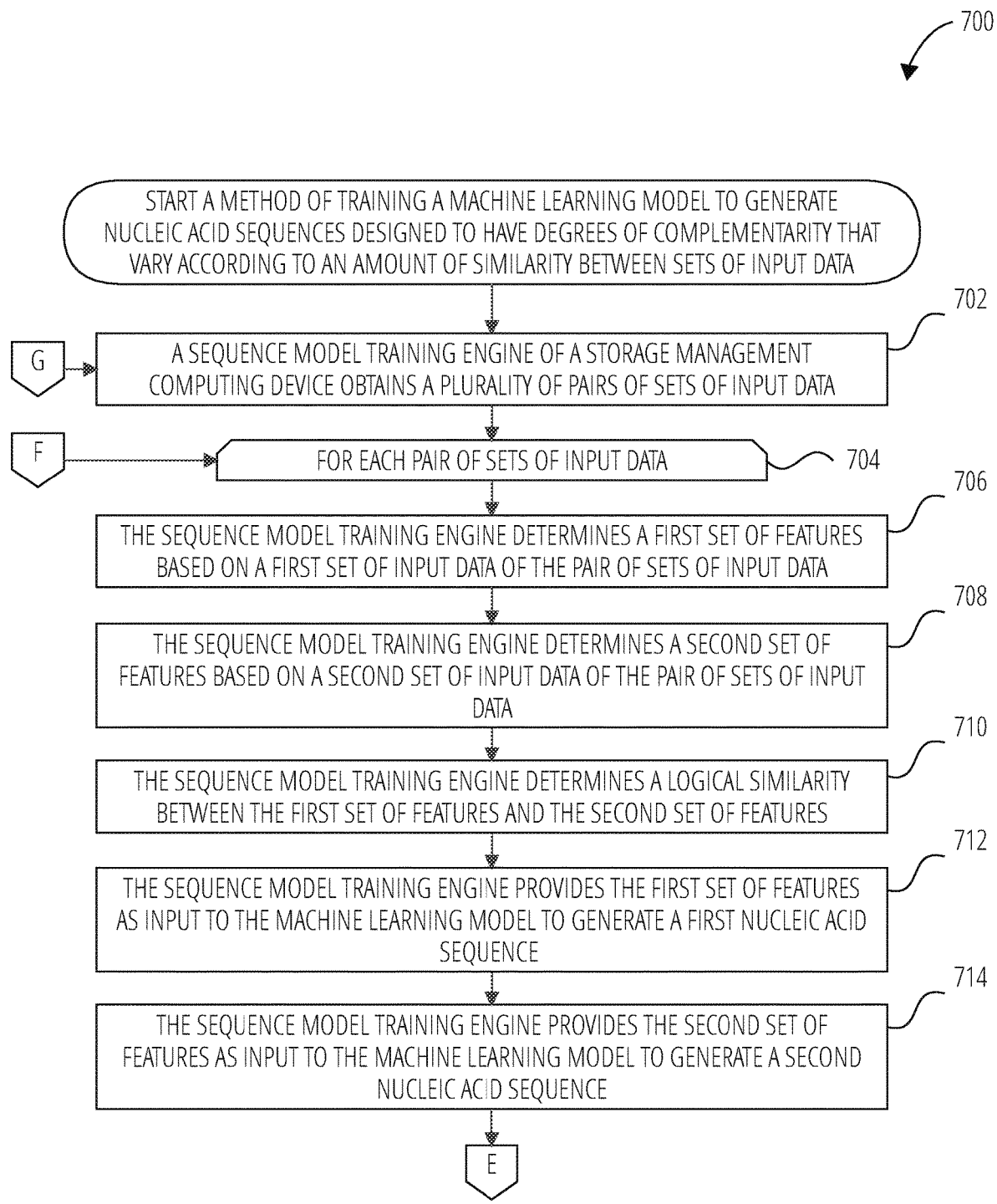
FIG. 7-FIG. 8 are a flowchart that illustrates a non-limiting example embodiment of a method of training a machine learning model to generate nucleic acid sequences designed to have degrees of complementarity that vary according to an amount of similarity between sets of input data, according to various aspects of the present disclosure.
Figure 8:
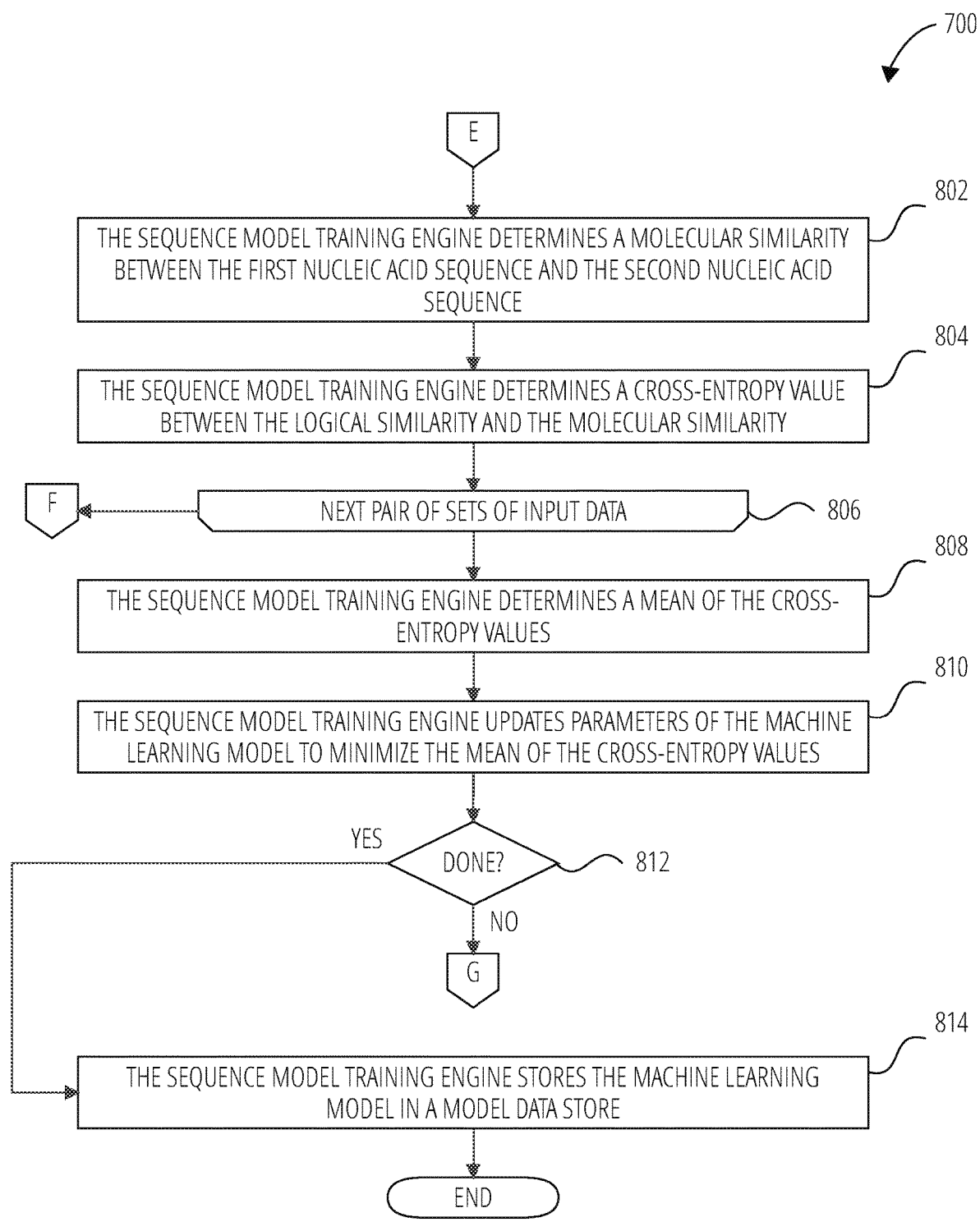

FIG. 7-FIG. 8 are a flowchart that illustrates a non-limiting example embodiment of a method of training a machine learning model to generate nucleic acid sequences designed to have degrees of complementarity that vary according to an amount of similarity between sets of input data, according to various aspects of the present disclosure. In the method 700 illustrated and described herein, the data sets are images, however, in other embodiments, the data sets could be text or any other type of data sets for which an automated technique for determining a logical similarity may be performed (or for which a significant amount of data with manually tagged similarity values is available).

Our general feature encoding strategy is inspired by semantic hashing, where a deep neural network transforms an input feature space into an output address space where similar items are "close" together. In some embodiments of the present disclosure, a neural network sequence encoder is used that takes a 10-dimensional image feature vector that is a dimensionality-reduced representation of the activations of the FC2 layer of VG16, and outputs DNA sequences that are close together if and only if the feature vectors are close together. A pair of query and target sequences are close if their hybridization reaction has a high thermodynamic yield: the proportion of target molecules that are converted into a query-target duplex.

From a start block, the method 700 proceeds to block 702, where a sequence model training engine 326 of a storage management computing device 312 obtains a plurality of pairs of sets of input data. The plurality of pairs of sets of input data may be obtained via a network, via a removable computer-readable medium, or via any other suitable technique. The plurality of pairs of sets of input data may be obtained from any suitable source. For example, a plurality of pairs of images may be obtained from the Caltech-256 dataset. In some embodiments, the sets of input data may be obtained as individuals, and may be randomly paired together by the sequence model training engine 326.

The method 700 then proceeds to a for-loop defined between a for-loop start block 704 and a for-loop end block 806, wherein each pair of sets of input data of the plurality of pairs of sets of input data is processed to determine whether the machine learning model generates sequences for the sets of input data with a degree of molecular similarity that is correlated with a logical similarity between the sets of input data.

From the for-loop start block 704, the method 700 proceeds to block 706, where the sequence model training engine 326 determines a first set of features based on a first set of input data of the pair of sets of input data, and at block 708, the sequence model training engine 326 determines a second set of features based on a second set of input data of the pair of sets of input data. Any suitable technique may be used to determine the sets of features, though the same technique will typically be used to determine the first set of features and the second set of features. In some embodiments, a set of features may be obtained from an image by processing the image with the VGG16 convolutional neural network, extracting the activations from the FC2 layer, and performing dimensionality reduction on the activations. In some embodiments, principal component analysis (PCA) may be used to reduce the activations to the ten principal components in order to obtain a set of ten features.

At block 710, the sequence model training engine 326 determines a logical similarity between the first set of features and the second set of features. A semantic notion of image "similarity" can be mapped to a real-valued number by computing the Euclidean distance between two sets of features. However, to use a cross-entropy loss function to optimize the machine learning model, image pairs should be labeled with a binary label (e.g., either "similar" or "not similar"). In some embodiments, a binary label may be applied using a Euclidean distance between sets of features by applying a predetermined threshold to the Euclidean distance. To a certain extent, similarity may be a subjective determination, and so, determination of an appropriate threshold for the Euclidean distance may be a subjective process. In some embodiments, a predetermined threshold of 0.2 for the Euclidean distance between sets of features determined via the VGG16+PCA technique described above may be appropriate. In some embodiments, other thresholds, including but not limited to thresholds within a range of 0.15 to 0.25, may be appropriate.

At block 712, the sequence model training engine 326 provides the first set of features as input to the machine learning model to generate a first nucleic acid sequence, and at block 714, the sequence model training engine 326 provides the second set of features as input to the machine learning model to generate a second nucleic acid sequence. In some embodiments, on an initial execution of block 712 and block 714, the machine learning model may have one or more optimizable layers with parameters that are initialized with random values. In some embodiments, on an initial execution of block 712 and block 714, the machine learning model may have one or more optimizable layers with parameters that are initialized with values from a previous execution of method 700.

The method 700 then proceeds to a continuation terminal ("terminal E"). From terminal E (FIG. 8), the method 700 proceeds to block 802, where the sequence model training engine 326 determines a molecular similarity between the first nucleic acid sequence and the second nucleic acid sequence. At block 804, the sequence model training engine 326 determines a cross-entropy value between the logical similarity and the molecular similarity. The method 700 then proceeds to the for-loop end block 806.

In some embodiments, the measure of molecular similarity between the first nucleic acid sequence and the second nucleic acid sequence is the thermodynamic yield or hybridization yield when the first nucleic acid sequence and a reverse complement sequence of the second nucleic acid sequence are combined. Thermodynamic yield can be calculated accurately by using the multi-stranded partition function, which is used by tools such as NUPACK. Unfortunately, this calculation is expensive, and because it is not differentiable it cannot be used directly to train a machine learning model.

Figure 9:
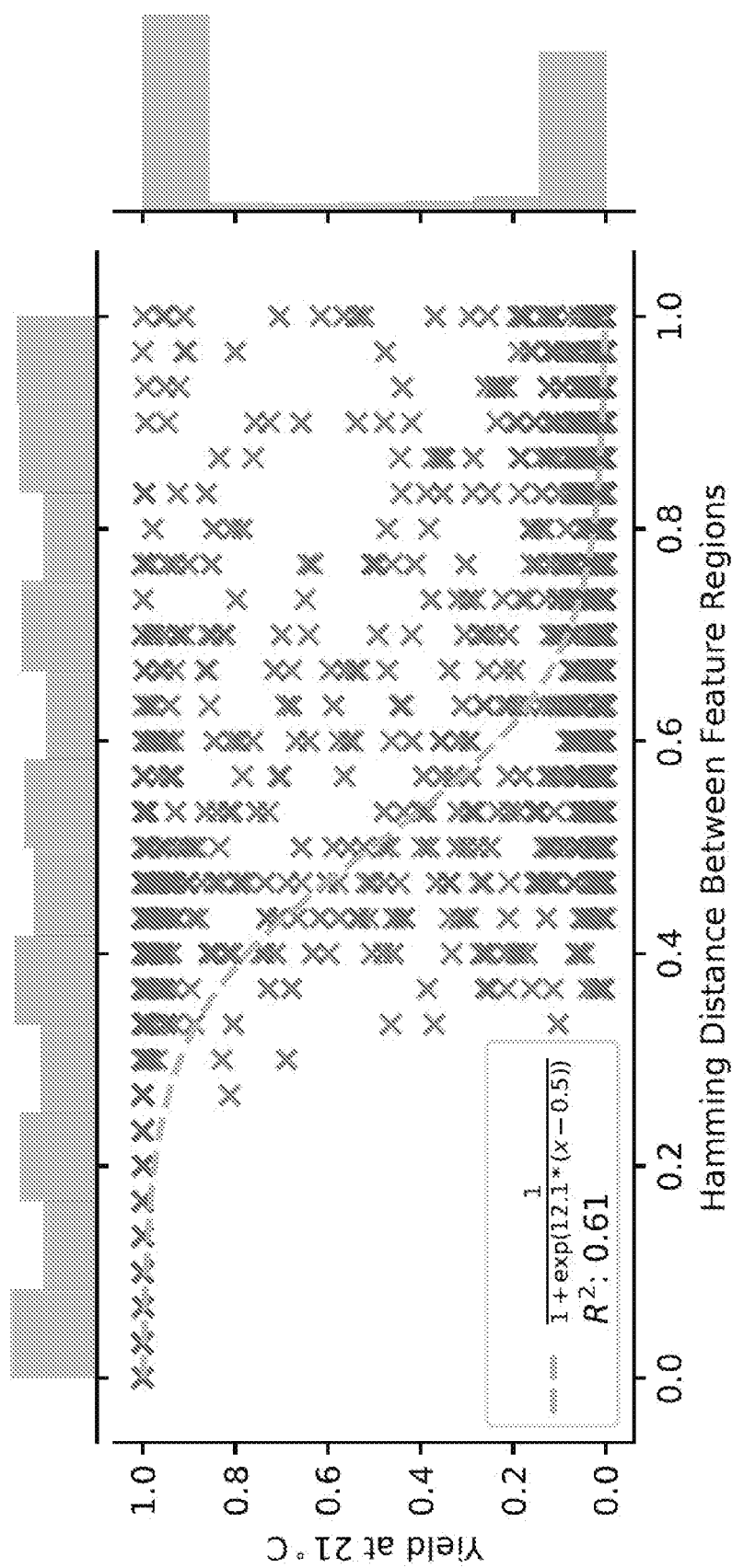
FIG. 9 is a chart that illustrates the relationship between yield and Hamming distance for 2000 pairs of nucleic acid sequences with feature regions of length 30, as calculated using the multi-stranded partition function, according to various aspects of the present disclosure.

One approximation that could be used for the thermodynamic yield is the Hamming distance between the first nucleic acid sequence and the second nucleic acid sequence. FIG. 9 is a chart that illustrates the relationship between yield and Hamming distance for 2000 pairs of nucleic acid sequences with feature regions of length 30, as calculated using the multi-stranded partition function, according to various aspects of the present disclosure. The dashed line shows the best sigmoid fit to the simulations. FIG. 9 shows that the yield and the Hamming distance have a noisy sigmoid relationship, which a function of the type:

$$f(x) = \frac{1}{1 + \exp(ax - b)}$$

The best fit line provides us with a simple approximation of thermodynamic yield in terms of the Hamming distance. One drawback of using the Hamming distance is that this approximation is less accurate for higher Hamming distances. Other drawbacks are that computing the Hamming distance requires discrete operations and is also not differentiable. What is needed are alternative representations of DNA sequences and a continuous approximation of Hamming distance that can be used to train a machine learning model.

Figure 10:
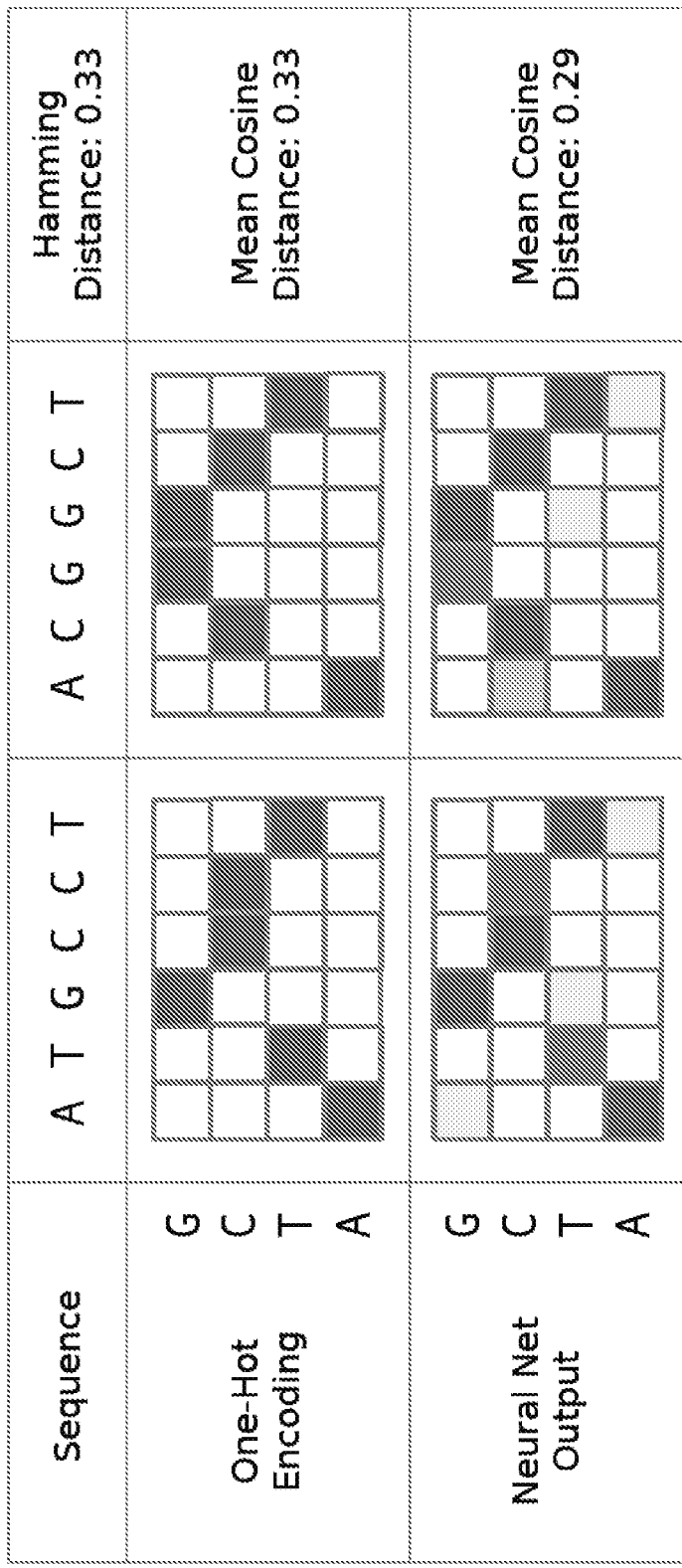
FIG. 10 is a chart that illustrates one-hot encodings of two six-nucleotide long sequences according to various aspects of the present disclosure.

In some embodiments of the present disclosure, DNA sequences are represented with a "one-hot" encoding, where each position is represented by a four-channel vector, and each channel corresponds to a base. For instance, if that base is an A, then the channel corresponding to A will have a value of one, and the other channels will be zero. FIG. 10 is a chart that illustrates one-hot encodings of two six-nucleotide long sequences according to various aspects of the present disclosure. At each position, the one-hot encodings can be compared by computing the cosine distance between them. Given two vectors u and v, the cosine distance between the two vectors may be given as:

$$d(u, v) = 1 - \frac{u \cdot v}{\|u\|\|v\|}$$

If they represent different bases, the representations will be orthogonal, and the cosine distance will be one. If they represent the same base, the cosine distance will be zero. Therefore, the mean cosine distance across positions will be equal to the mean number of mismatches, which is equivalent to the Hamming distance.

A neural network cannot output differentiable representations that are exactly one-hot, because this would require discretization. However, if the channel values at each position are sufficiently far apart, we can approximate a one-hot encoding by normalizing them with a softmax function. Given an N-dimensional vector u, the softmax function is defined element-wise as:

$$\text{softmax}(u)_i = \frac{e^{u_i}}{\sum_{j=1}^{N} e^{u_j}}$$

The softmax function pushes the maximum value towards one while pushing the other values towards zero. Furthermore, we can encourage the channel values to be far apart by using a hidden-layer activation function with a large output range, such as the rectified linear unit (ReLU) function:

ReLU(x)=max(x,0)

Figure 11:
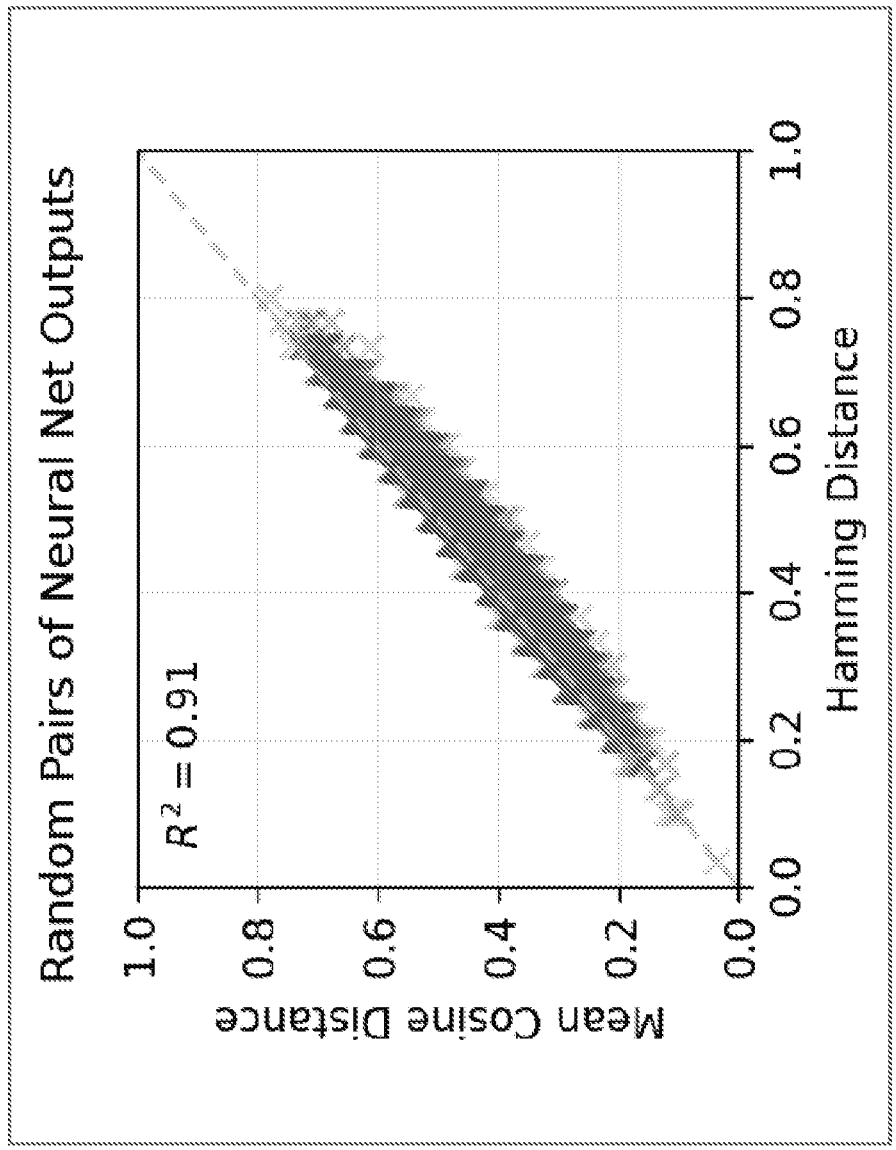
FIG. 11 is a chart that illustrates a relationship between the mean cosine distance and Hamming distance of pairs of outputs, for 10,000 pairs of random inputs to a randomly-initialized neural network with 10 input units, two ReLU hidden layers of 128 units each, and 30 four-channel softmax output units according to various aspects of the present disclosure.

FIG. 11 is a chart that illustrates a relationship between the mean cosine distance and Hamming distance of pairs of outputs, for 10,000 pairs of random inputs to a randomly-initialized neural network with 10 input units, two ReLU hidden layers of 128 units each, and 30 four-channel softmax output units according to various aspects of the present disclosure. The mean cosine distance between the neural network outputs closely follows the Hamming distance between their discretized counterparts, validating this approximation.

Figure 16:
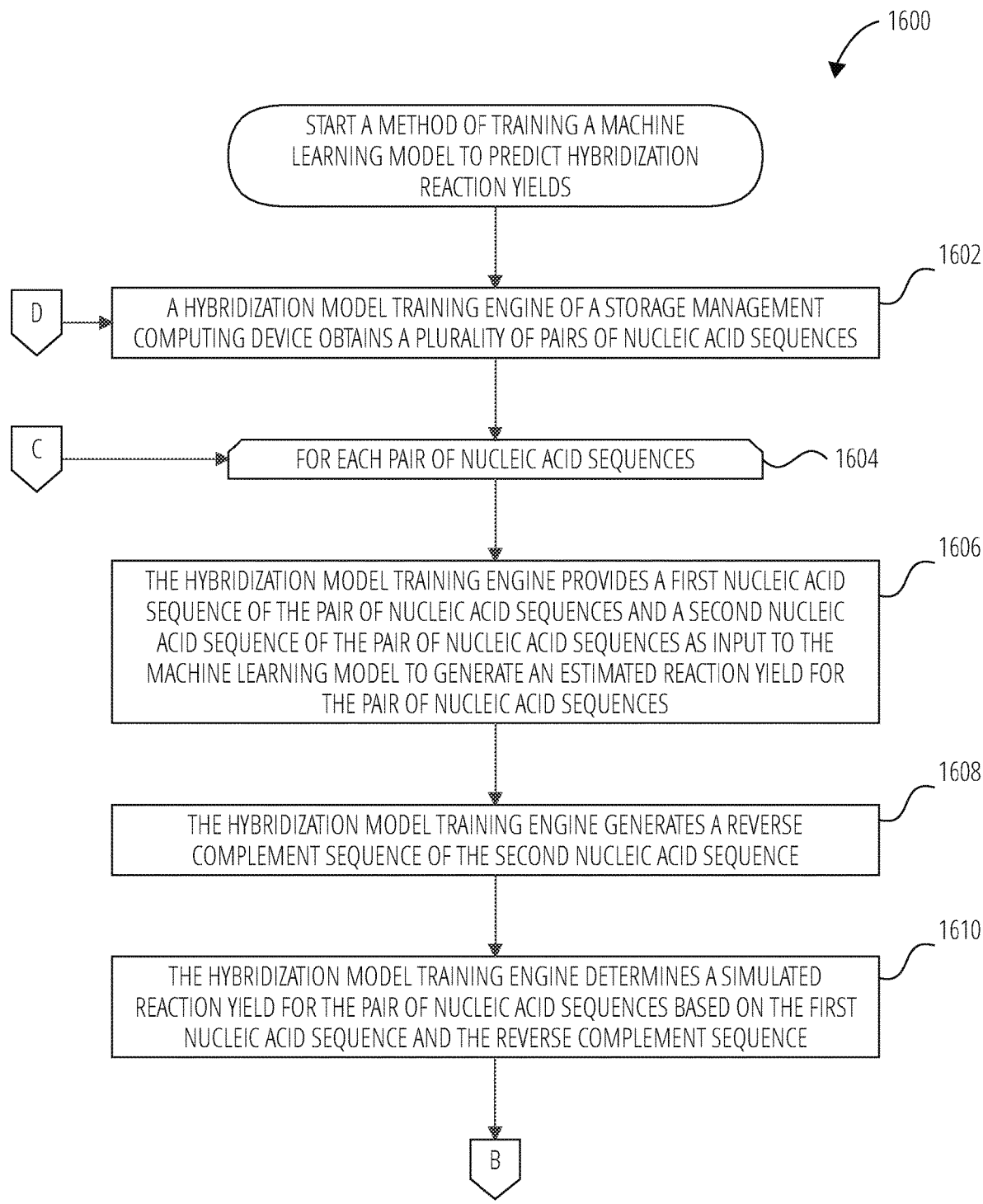
FIG. 16-FIG. 17 are a flowchart that illustrates a non-limiting example embodiment of a method of training a machine learning model to predict hybridization reaction yields according to various aspects of the present disclosure.
Figure 17:
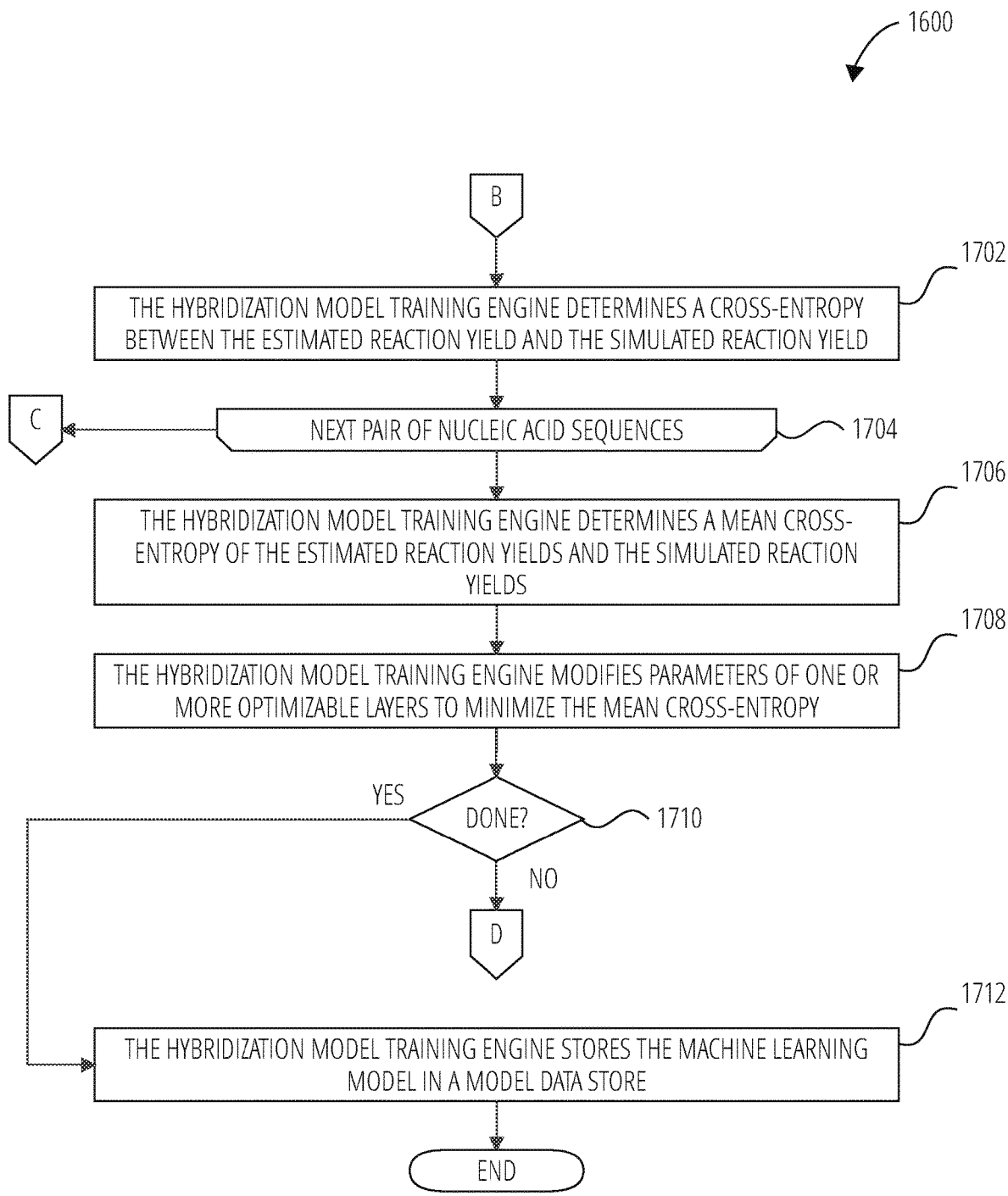

Composing the yield approximation with the Hamming distance approximation allows for the use of gradient descent to train any kind of neural-network-based machine learning model sequence encoder to generate good encodings for similarity search, given a suitable collection of data sets. Accordingly, in some embodiments, the molecular similarity between the first nucleic acid sequence and the second nucleic acid sequence may be determined using the mean cosine distance as discussed above. In some embodiments, a different type of hybridization yield predictor may be used. For example, in some embodiments, a differentiable machine learning model may be trained to predict hybridization yields, and the differentiable machine learning model may be used to determine the molecular similarity between the first nucleic acid sequence and the second nucleic acid sequence. One technique for training such a machine learning model is illustrated in FIG. 16-FIG. 17 and discussed in detail below.

Returning to FIG. 8, if further pairs of sets of input data remain to be processed, then the method 700 returns to for-loop start block 704 via a continuation terminal ("terminal F"). Otherwise, if all of the pairs of sets of input data have been processed, then the method 700 proceeds to block 808, where the sequence model training engine 326 determines a mean of the cross-entropy values. At block 810, the sequence model training engine 326 updates parameters of the machine learning model to minimize the mean of the cross-entropy values. Using the cross-entropy as a loss function penalizes similar images with low estimated reaction yield, dissimilar images with high estimated estimated reaction yield, and any estimated yields that are neither high nor low.

Figure 14:
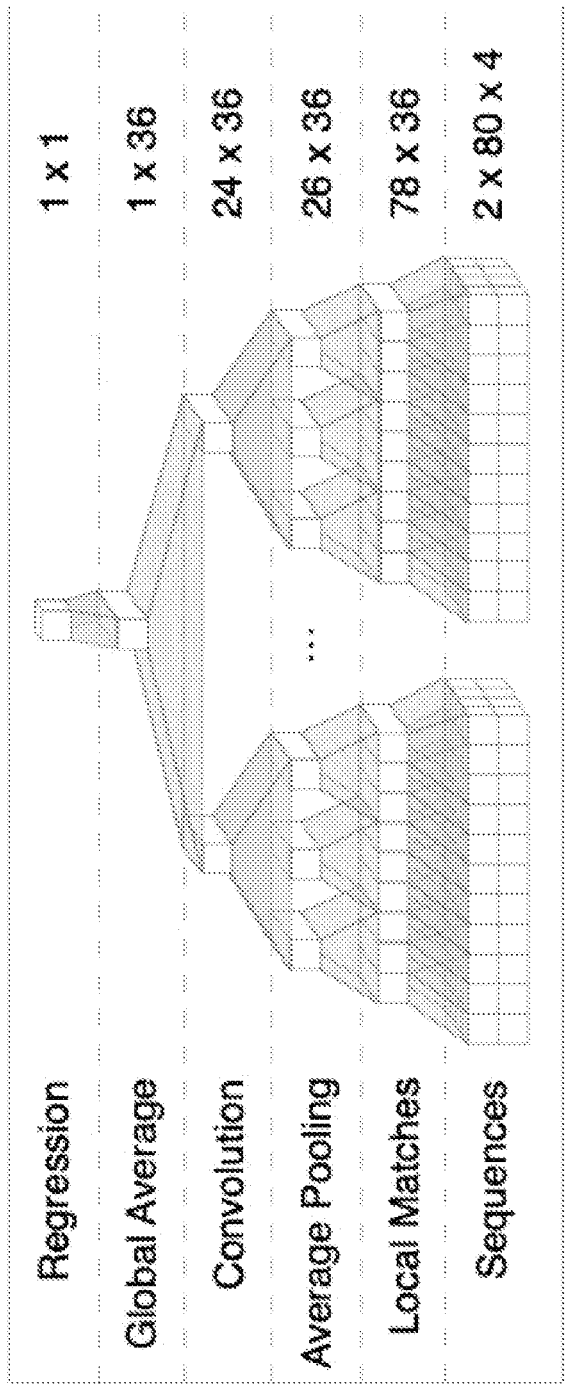
FIG. 14 illustrates a non-limiting example embodiment of a machine learning model for predicting hybridization reaction yields according to various aspects of the present disclosure.
Figure 15:
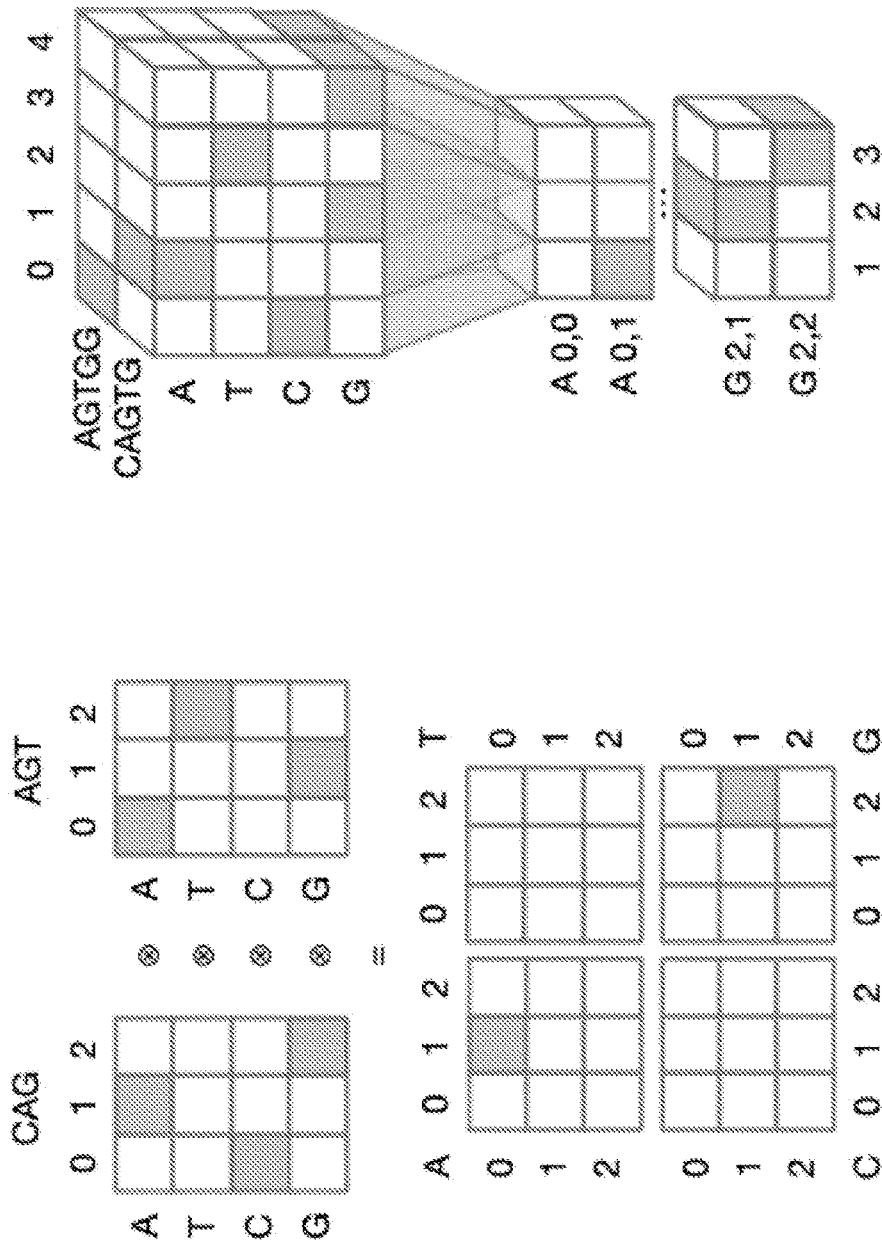
FIG. 15 illustrates a non-limiting example embodiment of the local match layer used by the machine learning model illustrated in FIG. 14, according to various aspects of the present disclosure.

Typically, gradient descent will be used to update these parameters based on the gradient of the cross-entropy loss with respect to the parameters. In some embodiments (such as embodiments that use a hybridization yield estimator as illustrated in FIG. 14 and FIG. 15, in order to use gradient descent, one-hot sequences representations that are not fully discrete are used. This can create positions with indeterminate bases, which may interfere with the hybridization yield predictor. To discretize the one-hot sequences as much as possible, we add an additional regularization term to the encoder to minimize the per-position entropy of the one-hot sequences. It is advisable to gently apply this regularization to avoid explosion of the gradients.

At decision block 812, a determination is made regarding whether optimization of the machine learning model is complete. Typically, this determination is based on a number of times the method 700 has processed the for-loop between for-loop start block 704 and for-loop end block 806, though any other suitable technique, including but not limited to determining whether performance of the machine learning model has converged, may be used.

If the determination results in a finding that optimization of the machine learning model is not complete, then the result of decision block 812 is NO, and the method 700 returns to block 702 via a continuation terminal ("terminal G"). If the determination results in a finding that optimization of the machine learning model is complete, then the result of decision block 812 is YES, and the method 700 proceeds to block 814. At block 814, the sequence model training engine 326 stores the machine learning model in a model data store 316. The sequence model training engine 326 may transmit the machine learning model to the model data store 316 using any suitable technique, including but not limited to storing the machine learning model directly on a computer-readable medium accessible to the sequence model training engine 326, and transmitting the machine learning model to the model data store 316 via a network.

The method 700 then proceeds to an end block and terminates.

Figure 12:
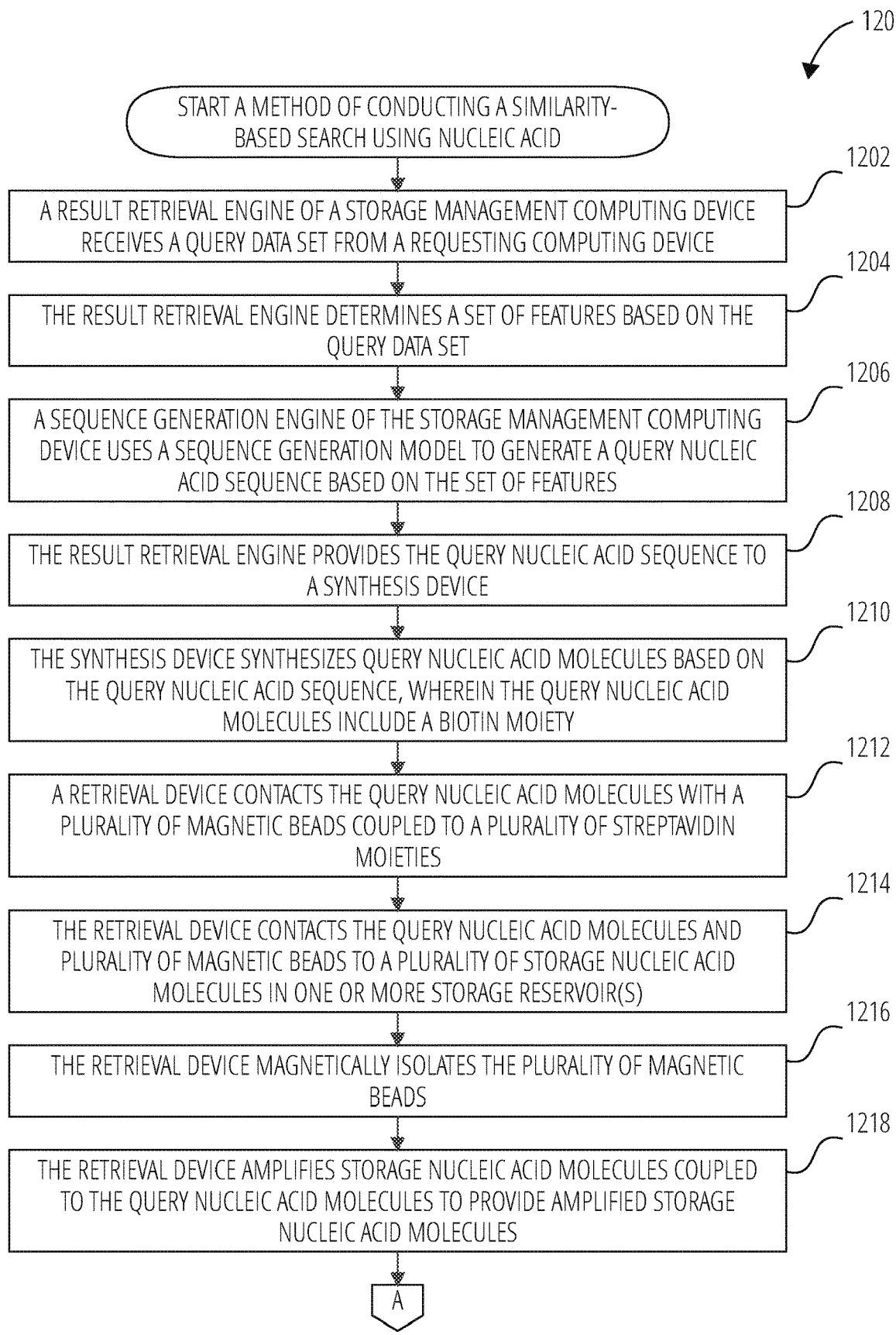
FIG. 12-FIG. 13 are a flowchart that illustrates a non-limiting example embodiment of a method of conducting a similarity-based search using nucleic acid according to various aspects of the present disclosure.
Figure 13:
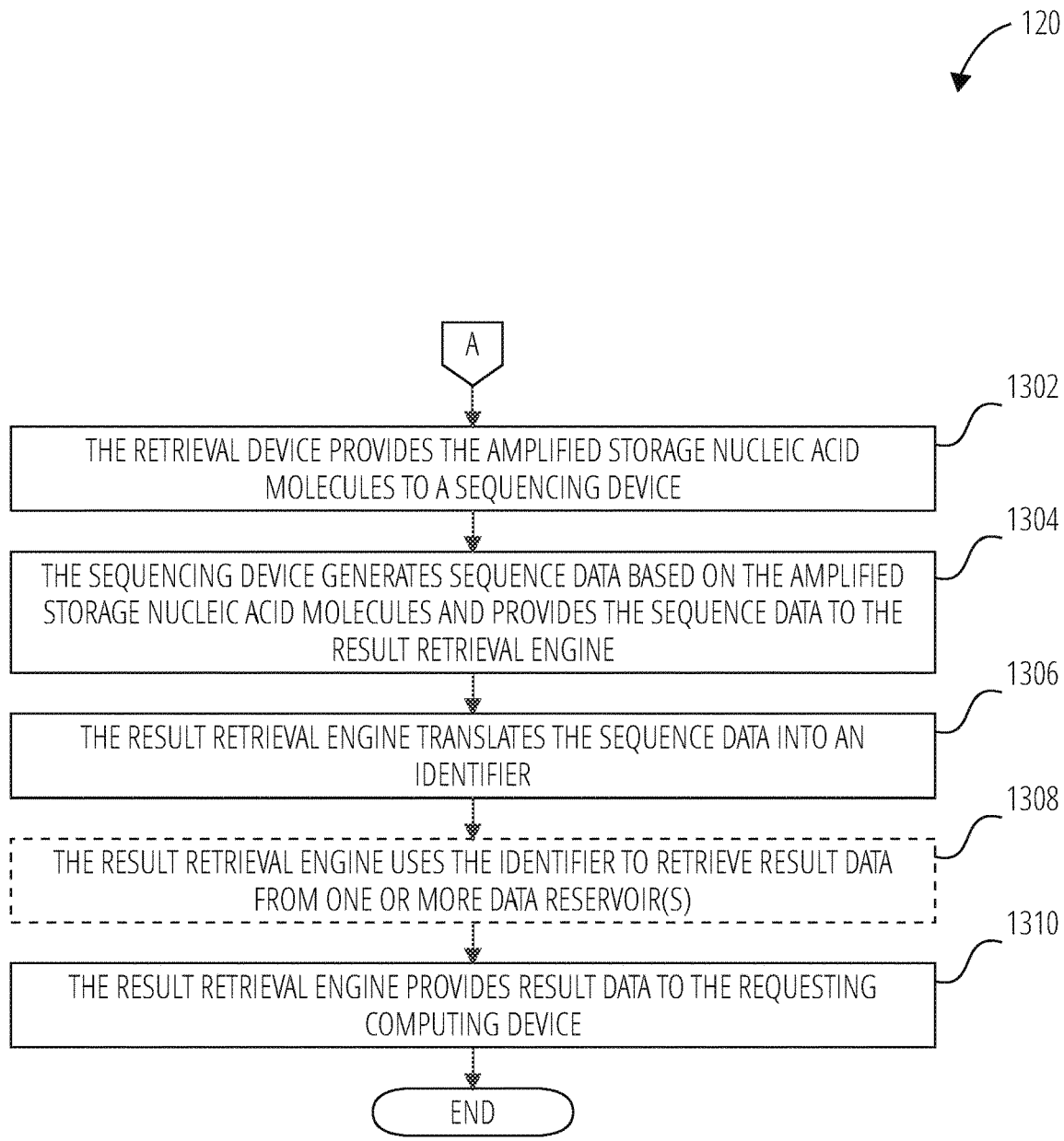

FIG. 12-FIG. 13 are a flowchart that illustrates a non-limiting example embodiment of a method of conducting a similarity-based search using nucleic acid according to various aspects of the present disclosure. In the method 1200, a query data set is received and a search is conducted using DNA to retrieve results that are similar to the query data set.

From a start block, the method 1200 proceeds to block 1202, where a result retrieval engine 320 of a storage management computing device 312 receives a query data set from a requesting computing device. The query data set may be an image, a document, or any other data set for which similar data sets are desired to be identified.

At block 1204, the result retrieval engine 320 determines a set of features based on the query data set. Any suitable technique may be used to determine the set of features that represents the query data set. The technique used should match a technique used to determine sets of features for the stored data sets, and may be different based on the type of data represented by the data sets. For example, in some embodiments in which the query data set is an image, the set of features may be determined by processing the query data set using a VGG16 convolutional neural network trained on an image classification task, and extracting the activations from the FC2 layer. The activations from the FC2 layer may then be further processed, such as by performing dimensionality reduction using any suitable technique. In some embodiments, dimensionality reduction may be performed by using principal component analysis (PCA) to reduce the dimensionality of the activations from the FC2 layer by any suitable amount. In some embodiments, PCA may be used to obtain the 10 principal components of the activations from the FC2 layer. This number of principal components may provide a reasonable balance between the detail represented in the features versus the efficiency of the further computations.

At block 1206, a sequence generation engine 324 of the storage management computing device 312 uses a sequence generation model to generate a query nucleic acid sequence based on the set of features. The sequence generation model may be retrieved from the model data store 316 by the sequence generation engine 324.

The sequence generation model is trained to generate nucleic acid sequences based on sets of features such that similarities between multiple sets of features are reflected in similarities between the generated nucleic acid sequences. In other words, if two sets of features are similar to each other, the sequence generation model will generate nucleic acid sequences that are similar to each other, and if two sets of features are not similar to each other, the sequence generation model will generate nucleic acid sequences that are not similar to each other. The degree of similarity between the sets of features is also reflected in the degree of similarity between the nucleic acid sequences—sets of features that are more similar will result in nucleic acid sequences that are more similar, while sets of features that are less similar will result in nucleic acid sequences that are less similar. In some embodiments, the degree of similarity between the nucleic acid sequences is reflected in the hybridization yield between nucleic acid molecules generated based on the nucleic acid sequences (or a first nucleic acid sequence and the reverse complement sequence of a second nucleic acid sequence), such that nucleic acid molecules based on similar nucleic acid sequences are more likely to hybridize with each other than nucleic acid molecules based on dissimilar nucleic acid sequences, to a degree that varies based on the degree of similarity. One example of a method of training a sequence generation model is illustrated in FIG. 7-FIG. 8 and described in further detail below.

At block 1208, the result retrieval engine 320 provides the query nucleic acid sequence to a synthesis device 302. The result retrieval engine 320 may transmit the query nucleic acid sequence to the synthesis device 302 over a network, by transferring a removable computer-readable medium between the storage management computing device 312 and the synthesis device 302, or via any other suitable technique.

At block 1210, the synthesis device 302 synthesizes query nucleic acid molecules based on the query nucleic acid sequence, wherein the query nucleic acid molecules include a biotin moiety. The synthesis device 302 may directly synthesize multiple query nucleic acid molecules, or may increase the volume of generated query nucleic acid molecules using PCR or any other suitable technique. In some embodiments, the synthesis device 302 may be configured to synthesize a reverse complement of the provided query nucleic acid sequence. In some embodiments, the result retrieval engine 320 may convert the query nucleic acid sequence to its reverse complement before transmitting it to the synthesis device 302. In some embodiments, the sequence generation model may be configured to produce a reverse complement sequence, such that the output of the sequence generation model can directly be used within the query nucleic acid molecules to hybridize with the storage nucleic acid molecules.

In some embodiments, the result retrieval engine 320 may add the biotin moiety to the query nucleic acid sequence before providing the query nucleic acid sequence to the synthesis device 302. In some embodiments, the query nucleic acid molecules may also include a reverse primer, which may also be added to the query nucleic acid sequence by the synthesis device 302 before transmitting the query nucleic acid sequence to the synthesis device 302. In some embodiments, instead of adding the biotin moiety and/or reverse primer to the query nucleic acid sequence to be synthesized, the biotin moiety and/or reverse primer may be added to the synthesized query nucleic acid molecules by annealing or other technique. As discussed above, FIG. 2 illustrates a non-limiting example embodiment of a query nucleic acid molecule 204 according to various aspects of the present disclosure.

At block 1212, a retrieval device 306 contacts the query nucleic acid molecule with a plurality of magnetic beads coupled to a plurality of streptavidin moieties. In some embodiments, the retrieval device 306 may physically transport the query nucleic acid molecules to a reservoir in which the plurality of magnetic beads reside, and may cause the query nucleic acid molecules to be bonded to the plurality of magnetic beads using any known suitable technique.

At block 1214, the retrieval device 306 contacts the query nucleic acid molecule and plurality of magnetic beads to a plurality of storage nucleic acid molecules in one or more storage reservoir(s) 308. In some embodiments, the retrieval device 306 may physically transport the plurality of storage nucleic acid molecules and the plurality of magnetic beads to a reservoir, and may physically transport a sample from the one or more storage reservoir(s) 308 to the same reservoir. The retrieval device 306 may then cause the query nucleic acid molecules and the storage nucleic acid molecules to be annealed or otherwise hybridized using any suitable technique.

At block 1216, the retrieval device 306 magnetically isolates the plurality of magnetic beads. In some embodiments, the retrieval device 306 may physically transport the reservoir in which the hybridized query nucleic acid molecules and storage nucleic acid molecules reside to a magnetic rack or other device that will cause the magnetic isolation of the plurality of magnetic beads. In some embodiments, the retrieval device 306 may also remove a supernatant containing non-captured DNA.

At block 1218, the retrieval device 306 amplifies storage nucleic acid molecules coupled to the query nucleic acid molecules to provide amplified storage nucleic acid molecules. The retrieval device 306 may use any suitable technique, including but not limited to PCR, to provide the amplified storage nucleic acid molecules.

The method 1200 then proceeds to a continuation terminal ("terminal A"). From terminal A (FIG. 13), the method 1200 proceeds to block 1302. At block 1302, the retrieval device 306 provides the amplified storage nucleic acid molecules to a sequencing device 304. In some embodiments, the retrieval device 306 may physically transport the amplified storage nucleic acid molecules to an input of the sequencing device 304. In some embodiments, the retrieval device 306 may also prepare the amplified storage nucleic acid molecules for the sequencing device 304, such as by ligating the amplified storage nucleic acid molecules with a sequencing adapter designed for the sequencing device 304.

At block 1304, the sequencing device 304 generates sequence data based on the amplified storage nucleic acid molecules and provides the sequence data to the result retrieval engine 320. The sequencing device 304 may use any suitable technique for generating the sequence data, and may provide the sequence data to the result retrieval engine 320 using any suitable technique, including but not limited to transmitting the sequence data via a network, or exchanging a removable computer-readable medium with the storage management computing device 312.

At block 1306, the result retrieval engine 320 translates the sequence data into one or more identifiers. In some embodiments, the sequence data may represent one or more storage nucleic acid molecules such as storage nucleic acid molecule 202 as illustrated in FIG. 2. In such embodiments, the result retrieval engine 320 may translate the sequence data into identifiers by finding the d(T) portions of the storage nucleic acid molecules in the sequence data, and using the d(T) portions as the identifiers. In some embodiments, the result retrieval engine 320 may further translate the d(T) portions, such as by converting the sequence of the d(T) portions to a binary or numeric representations, to determine the identifiers. In some embodiments, the result retrieval engine 320 may determine or provide identifiers that are present in a percentage of the amplified storage nucleic acid molecules that meets a predetermined threshold percentage, such that multiple results may be returned, but that only the storage nucleic acid molecules that hybridized with the query nucleic acid molecules at the highest rates are included in the results.

In some embodiments, the d(T) portion of the identifier (or the further converted version thereof) may be the result data. However, in other embodiments, the identifier (or the further converted version thereof) may be used to retrieve a data set from storage such as one or more data reservoir 310. Accordingly, at optional block 1308, the result retrieval engine 320 uses the identifier to retrieve result data from one or more data reservoir(s) 310. In some embodiments, the identifier may be attached to a primer to amplify data nucleic acid molecules that have matching identifiers in order to retrieve data sets from the data reservoir(s) 310. In some embodiments, the identifier may itself serve as an amplification primer without further processing.

At block 1310, the result retrieval engine 320 provides the result data to the requesting computing device. As discussed above, the result data may be one or more data sets or one or more identifiers usable to retrieve one or more data sets.

The method 1200 then proceeds to an end block and terminates.

As discussed above, hybridization reaction yields between two nucleic acid sequences may be predicted by a machine learning model. FIG. 14 illustrates a non-limiting example embodiment of a machine learning model for predicting hybridization reaction yields according to various aspects of the present disclosure.

The illustrated machine learning model takes a pair of one-hot sequence representations and produces an estimate of the yield of the hybridization reaction between a nucleic acid molecule represented by the first nucleic acid sequence and a nucleic acid molecule represented by the reverse complement sequence of the second nucleic acid sequence. The illustrated machine learning model uses a novel local match layer that produces vectors of possible matches between each window of k-mers. As illustrated, 3-mers are used, but in some embodiments, k-mers of other size may be used. The use of windows of k-mers as illustrated encourages the predictor to make use of any unaligned matches between the two sequences.

An average pooling layer provides the output of the local match layer to a fully-connected convolutional layer. The output of the convolutional layer is provided to a global average layer, and a regression layer processes the output of the global average layer to generate the yield prediction. As shown, the convolutional layer and the regression layer are optimizable layers.

FIG. 15 illustrates a non-limiting example embodiment of the local match layer used by the machine learning model illustrated in FIG. 14, according to various aspects of the present disclosure. As shown, the outer product of each channel in each pair of 3-mers is obtained. The outer products then slide over each adjacent pair of 3-mers to generate the output of the local match layer.

FIG. 16-FIG. 17 are a flowchart that illustrates a non-limiting example embodiment of a method of training a machine learning model to predict hybridization reaction yields according to various aspects of the present disclosure. Such a machine learning model could be used in the method 700 discussed above, or could be separately useful outside of the context of method 700. In some embodiments, the method 1600 may be performed alongside the method 700 for training the sequence encoder, with an overall method alternating back and forth between encoder and predictor training phases.

From a start block, the method 1600 proceeds to block 1602, where a hybridization model training engine 322 of a storage management computing device 312 obtains a plurality of pairs of nucleic acid sequences. Any suitable technique for obtaining the plurality of pairs of nucleic acid sequences may be used. In some embodiments, the plurality of pairs of nucleic acid sequences could represent sets of features generated based on a plurality of data sets. In some embodiments, the plurality of pairs of nucleic acid sequences could be randomly selected from a set of random nucleic acid sequences. In some embodiments, the nucleic acid sequences may be provided as one-hot sequence representations, which may or may not be discretized.

The method 1600 then proceeds to a for-loop defined between a for-loop start block 1604 and a for-loop end block 1704 wherein each pair of nucleic acid sequences in the plurality of pairs of nucleic acid sequences is processed to compare a hybridization reaction yield estimated by the machine learning model to a simulated hybridization reaction yield.

From the for-loop start block 1604, the method 1600 proceeds to block 1606, where the hybridization model training engine 322 provides a first nucleic acid sequence of the pair of nucleic acid sequences and a second nucleic acid sequence of the pair of nucleic acid sequences as input to the machine learning model to generate an estimated reaction yield for the pair of nucleic acid sequences. Any structure for the machine learning model may be used, including but not limited to the structure illustrated in FIG. 14 and FIG. 15 and described above.

At block 1608, the hybridization model training engine 322 generates a reverse complement sequence of the second nucleic acid sequence, and at block 1610, the hybridization model training engine 322 determines a simulated reaction yield for the pair of nucleic acid sequences based on the first nucleic acid sequence and the reverse complement sequence. In some embodiments, if the nucleic acid sequences are provided as one-hot sequence representations that are not discrete, the sequences may be discretized before block 1610. Any suitable technique for determining the simulated reaction yield may be used, including but not limited to using the multi-stranded partition function of the NUPACK tool (or another tool).

The method 1600 then proceeds to a continuation terminal ("terminal B"). From terminal B (FIG. 17), the method 1600 proceeds to block 1702, where the hybridization model training engine 322 determines a cross-entropy value between the estimated reaction yield and the simulated reaction yield. The method 1600 then proceeds to the for-loop end block 1704. If further pairs of nucleic acid sequences remain to be processed, then the method 1600 returns to the for-loop start block 1604 via a continuation terminal ("terminal C"). Otherwise, if all of the pairs of nucleic acid sequences have been processed, then the method 1600 advances from the for-loop end block 1704 to block 1706.

At block 1706, the hybridization model training engine 322 determines a mean cross-entropy of the estimated reaction yields and the simulated reaction yields. At block 1708, the hybridization model training engine 322 modifies parameters of one or more optimizable layers to minimize the mean cross-entropy. Any suitable technique for modifying the parameters may be used, including gradient descent.

The method 1600 then advances to decision block 1710, where a determination is made regarding whether optimization of the optimizable layers of the machine learning model has been completed. Typically, this determination is based on a number of times the method 1600 has processed the for-loop between for-loop start block 1604 and for-loop end block 1704, though any other suitable technique, including but not limited to determining whether performance of the machine learning model has converged, may be used.

If the determination results in a finding that optimization of the optimizable layers has not yet been completed, then the result of decision block 1710 is NO, and the method 1600 returns to block 1602 via a continuation terminal ("terminal D") to continue the optimization process. If the determination results in a finding that the optimization of the optimizable layers is complete, then the result of decision block 1710 is YES, and the method 1600 proceeds to block 1712. At block 1712, the storage management computing device 312 stores the machine learning model in a model data store 316.

The method 1600 then proceeds to an end block and terminates.

Figure 18:
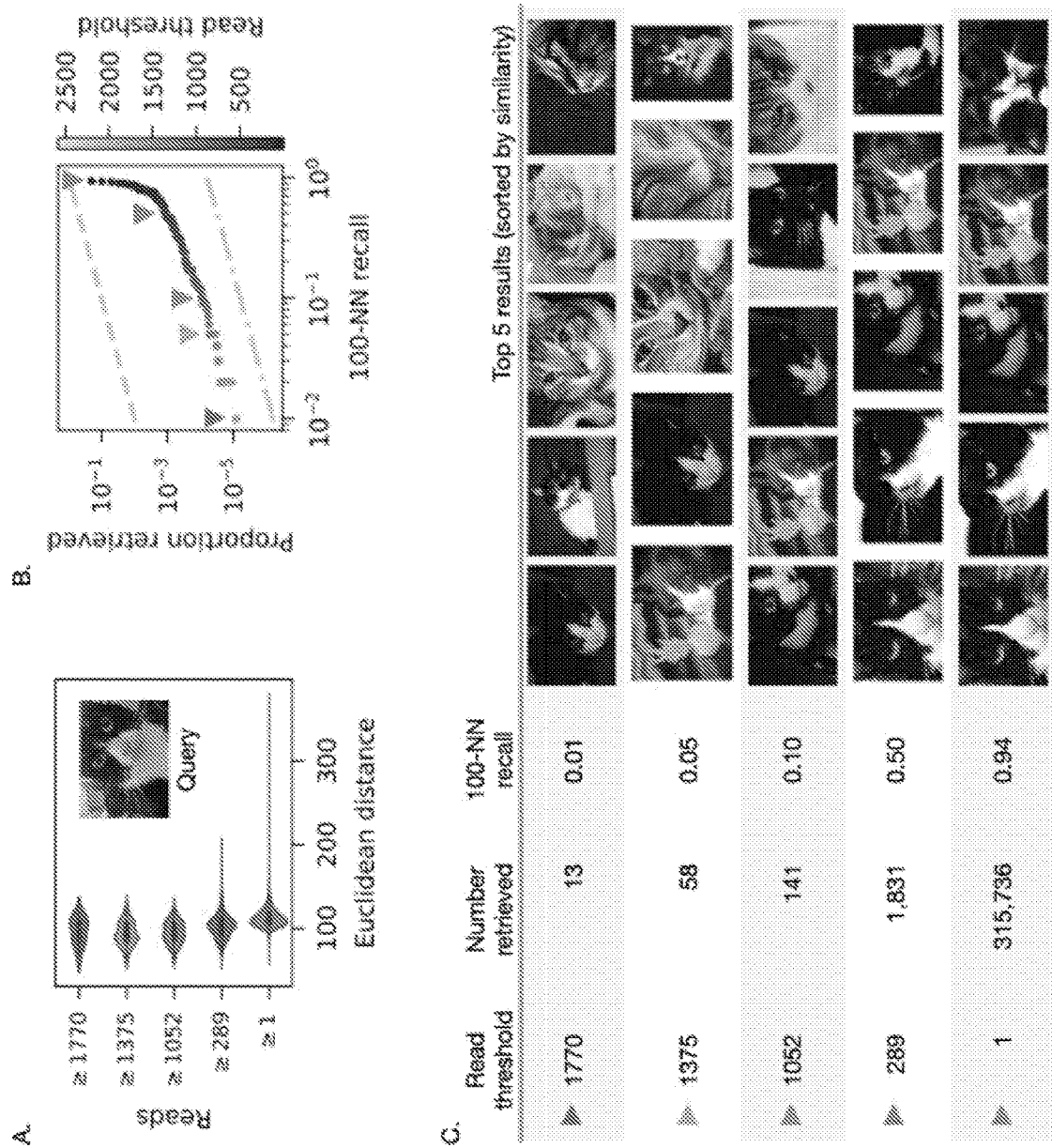
FIG. 18 illustrates experimental results for an embodiment of the present disclosure.

FIG. 18 illustrates experimental results for an embodiment of the present disclosure. Once the system 300 was trained, the encoder was used to transform a database of 1.6 million image feature vectors into DNA sequences. In addition to the encoded features, each image's sequence contains a unique, decodable barcode that can identify the sequence without using reference-based alignment, as well as conserved regions to facilitate amplification and processing via PCR (polymerase chain reaction). Each image's sequence is short enough to fit on a single synthesizable DNA oligomer. We ordered the database from Twist Bioscience, who synthesized all 1.6 million oligomers on a single chip using their array synthesis technology.

To conduct similarity search using a given query image, we ordered a biotinylated probe oligomer from IDT that contains the reverse complement of the query's encoded feature sequence. We anneal the probe with a sample of the database, and then separate the annealed target/query pairs from the database using streptavidin-conjugated magnetic beads. We then use high-throughput sequencing to reveal which database sequences persist in the filtered mixture, and measure how frequently each of them occur.

FIG. 18 shows the experimental results for a query conducted using an image of a cat. If we consider images with read counts above a certain threshold to be "retrieved", we can characterize the set of retrieved images for a variety of thresholds. Portion A of FIG. 18 shows that higher read counts are associated with sets of images that are closer to the query in Euclidean distance. We can quantitatively characterize the quality of a retrieved set by its recall of the 100 nearest neighbors; that is, the number of images in the set that are among the 100 most similar images to the query in the database. Portion B of FIG. 18 shows that, as the read threshold increases, the number of total images in the retrieved set drops very low before you begin to sacrifice nearest neighbor recall. We can also visually inspect the retrieved set by sorting its contents and displaying the most similar images. Portion C of FIG. 18 shows that, even with very aggressive filtering (down to only thirteen images out of 1.6 million), the retrieved set still contains images that are relevant to the query. Assuming that the read counts for each image are proportional to their concentrations in the filtered mixture, this means that the filtered mixture could be diluted about 1000×, conserving sequencing resources while still retrieving relevant images.

The performance of a similarity search algorithm can be summarized by the curve in Portion B of FIG. 18, which measures the proportion of the database that must be retrieved and sorted to achieve a particular nearest neighbor recall. The dashed line above the curve illustrates a "naive" algorithm that randomly samples the database. To retrieve half of the hundred nearest neighbors, it must retrieve half of the database. The dashed-and-dotted line below the curve illustrates a perfect "oracle" algorithm. To retrieve half of the hundred nearest neighbors, it would retrieve exactly those 50 images from the 1.6 million in the database.

Figure 19:
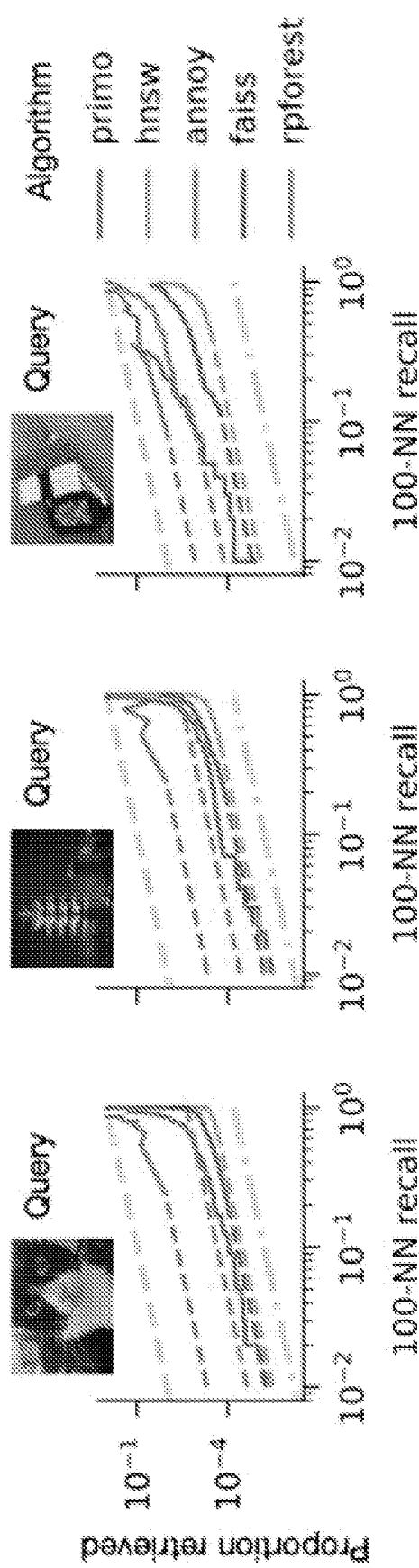
FIG. 19 places the curve from Portion B of FIG. 18 in context alongside several state-of-the-art in silico algorithms that were benchmarked using the same query and same database.

FIG. 19 places the curve from Portion B of FIG. 18 in context alongside several state-of-the-art in silico algorithms that were benchmarked using the same query and same database. Our experimental performance is comparable to the state-of-the-art, indicating that DNA-based similarity search is a viable technique for searching the databases of the future.

While illustrative embodiments have been illustrated and described, it will be appreciated that various changes can be made therein without departing from the spirit and scope of the invention.

What is claimed is:

1. A method of performing a search for information data sets similar to a query data set in a database that stores information in a plurality of storage nucleic acid molecules, the method comprising:
   determining a set of features based on the query data set;
   determining a query nucleic acid sequence based on the set of features, wherein a degree of complementarity with the query nucleic acid sequence is correlated with a degree of similarity with the set of features;
   synthesizing one or more query nucleic acid molecules based on the query nucleic acid sequence;
   contacting the one or more query nucleic acid molecules with the plurality of storage nucleic acid molecules so that the one or more query nucleic acid molecules hybridize with the plurality of storage nucleic acid molecules to a degree that varies based on a degree of similarity between the set of features based on the query data set and sets of features represented by the storage nucleic acid molecules;
   amplifying storage nucleic acid molecules coupled to the one or more query nucleic acid molecules to provide amplified storage nucleic acid molecules;
   generating sequence data based on the amplified storage nucleic acid molecules;
   translating the sequence data into result data for the search; and
   presenting the result data for the search sorted by similarity to the query data set.

2. The method of claim 1, wherein determining the set of features based on the query data set includes:
   processing the query data set using an artificial neural network; and
   extracting activations from a hidden layer of the artificial neural network.

3. The method of claim 2, wherein processing the query data set using an artificial neural network includes processing the query data set using a VGG16 convolutional neural network.

4. The method of claim 3, wherein extracting activations from the hidden layer of the artificial neural network includes extracting activations from an FC2 layer of the VGG16 convolutional neural network.

5. The method of claim 2, wherein determining the set of features based on the query data set further includes conducting dimensionality reduction on the activations to obtain the set of features.

6. The method of claim 5, wherein conducting dimensionality reduction on the activations to obtain the set of features includes performing principal component analysis (PCA) on the activations.

7. The method of claim 1, wherein determining the query nucleic acid sequence based on the set of features includes providing the set of features as input to a machine learning model trained to generate nucleic acid sequences designed to have degrees of complementarity that vary according to an amount of similarity between sets of features.

8. A computer-implemented method of conducting a similarity search using a nucleic acid data index, the method comprising:
   determining, by a computing device, a set of features based on a query data set;
   determining, by the computing device, a query nucleic acid sequence based on the set of features, wherein a degree of complementarity with the query nucleic acid sequence is correlated with a degree of similarity with the set of features;
   providing, by the computing device, the query nucleic acid sequence for synthesizing into a query nucleic acid molecule;
   receiving, by the computing device, sequencing data for molecules retrieved from a plurality of storage nucleic acid molecules using the query nucleic acid molecule;
   decoding, by the computing device, information stored in the sequencing data to obtain a plurality of search results; and
   presenting, by the computing device, the plurality of search results sorted by similarity to the query data set.

9. The method of claim 8, wherein determining the set of features based on the query data set includes:
   processing the query data set using an artificial neural network; and
   extracting activations from a hidden layer of the artificial neural network.

10. The method of claim 9, wherein processing the query data set using the artificial neural network includes processing the query data using a VGG16 convolutional neural network.

11. The method of claim 10, wherein extracting activations from the hidden layer of the artificial neural network includes extracting activations from an FC2 layer of the VGG16 convolutional neural network.

12. The method of claim 9, wherein determining the set of features based on the query data set further includes conducting dimensionality reduction on the extracted activations to determine the set of features.

13. The method of claim 12, wherein conducting dimensionality reduction on the extracted activations to determine the set of features includes performing principal component analysis (PCA) on the activations.

14. The method of claim 8, wherein determining the query nucleic acid sequence based on the set of features includes providing the set of features as input to a machine learning model trained to generate nucleic acid sequences designed to have degrees of complementarity that vary according to an amount of similarity between sets of features.

15. The method of claim 14, wherein the amount of similarity between sets of features is determined based on a Euclidean distance between the sets of features.

16. A system for performing a similarity search using nucleic acids, the system comprising:
- a nucleic acid synthesizer configured to synthesize nucleic acid molecules;
- a nucleic acid sequencer configured to generate a signal based upon a sequence of a nucleic acid;
- a plurality of storage nucleic acid molecules, wherein each of the plurality of storage nucleic acid molecules includes:
  - a payload sequence associated with a data object; and
  - a target sequence based on a set of features derived from the data object; and
- a controller operatively coupled to the nucleic acid synthesizer and the nucleic acid sequencer, the controller including logic that, in response to execution by the controller, causes the system to perform operations including:
  - converting a received query data set into a query nucleic acid sequence, the query nucleic acid sequence comprising a query sequence based on a set of features based on the query data set, wherein a degree of complementarity of the query sequence and a target sequence is based upon a Euclidean distance between the set of features based on the query data set and the set of features derived from the data object;
  - synthesizing one or more query nucleic acid molecules based on the query nucleic acid sequence with the nucleic acid synthesizer;
  - contacting the query nucleic acid molecule with the plurality of storage nucleic acid molecules so that one or more query nucleic acid molecules hybridize with the plurality of storage nucleic acid molecules to a degree that varies based on a degree of similarity between the set of features based on the query data set and the sets of features derived from the data objects;
  - amplifying storage nucleic acid molecules coupled to the one or more query nucleic acid molecules to provide amplified storage nucleic acid molecules;
  - generating sequence data with the nucleic acid sequencer based on the amplified storage nucleic acid molecules;
  - translating the sequence data into result data for the search; and
  - presenting the result data for the search sorted by similarity to the received query data set.

17. The system of claim 16, wherein a greater degree of complementarity between the query nucleic acid sequence and the target sequence corresponds to a shorter Euclidean distance between the set of features based on the query data set and the set of features derived from the data object.

18. The system of claim 16, further comprising a plurality of magnetic beads coupled to a plurality of streptavidin moieties;
- wherein the query nucleic acid molecule further comprises a biotin moiety coupled to the query sequence; and
- wherein the controller further includes logic that, in response to execution by the controller, causes the system to perform operations including:
  - contacting the query nucleic acid molecule with the plurality of magnetic beads;
  - magnetically isolating the plurality of magnetic beads; and
  - amplifying storage nucleic acid molecules coupled to the plurality of magnetic beads.

19. The system of claim 16, wherein the query sequence includes one or more base pairs complementary to base pairs of one or more of the forward primer and the reverse primer.

20. The system of claim 16, wherein the controller includes logic that, in response to execution by the controller, causes the system to perform operations including:
- synthesizing a storage nucleic acid molecule with the nucleic acid synthesizer, wherein the storage nucleic acid molecule comprises:
  - a payload sequence based on a data object; and
  - a target sequence based on a set of features derived from the data object.

* * * * *